US011103596B2

(12) United States Patent
Nathwani et al.

(10) Patent No.: US 11,103,596 B2
(45) Date of Patent: Aug. 31, 2021

(54) FABRY DISEASE GENE THERAPY

(71) Applicant: UCL Business LTD, London (GB)

(72) Inventors: Amit Nathwani, London (GB); Deepak Raj, London (GB)

(73) Assignee: UCL BUSINESS PLC, London (GB)

( * ) Notice: Subject to any disclaimer, the term of this patent is extended or adjusted under 35 U.S.C. 154(b) by 505 days.

(21) Appl. No.: 15/573,203

(22) PCT Filed: May 10, 2016

(86) PCT No.: PCT/GB2016/051328
§ 371 (c)(1),
(2) Date: Nov. 10, 2017

(87) PCT Pub. No.: WO2016/181122
PCT Pub. Date: Nov. 17, 2016

(65) Prior Publication Data
US 2018/0110878 A1   Apr. 26, 2018

(30) Foreign Application Priority Data

May 11, 2015   (GB) .................................... 1508025

(51) Int. Cl.
| | | |
|---|---|---|
| C12N 15/55 | (2006.01) | |
| C12N 9/40 | (2006.01) | |
| A61K 48/00 | (2006.01) | |
| C12N 15/86 | (2006.01) | |
| C12N 15/113 | (2010.01) | |
| A61P 3/00 | (2006.01) | |
| A61K 38/47 | (2006.01) | |

(52) U.S. Cl.
CPC .......... *A61K 48/0058* (2013.01); *A61K 38/47* (2013.01); *A61P 3/00* (2018.01); *C12N 9/2465* (2013.01); *C12N 15/86* (2013.01); *A01K 2217/075* (2013.01); *C12N 2750/14143* (2013.01); *C12N 2750/14171* (2013.01); *C12N 2800/22* (2013.01)

(58) Field of Classification Search
None
See application file for complete search history.

(56) References Cited

U.S. PATENT DOCUMENTS

| | | | |
|---|---|---|---|
| 6,066,626 A | 5/2000 | Yew et al. | |
| 6,083,725 A | 7/2000 | Selden et al. | |
| 6,210,666 B1 | 4/2001 | Miyamura | |
| 6,274,597 B1 | 8/2001 | Fan et al. | |
| 6,303,371 B1 | 10/2001 | Wadsworth | |
| 6,461,609 B1 | 10/2002 | Calhoun et al. | |
| 6,589,964 B2 | 7/2003 | Fan et al. | |
| 6,599,919 B2 | 7/2003 | Fan et al. | |
| 6,667,174 B2 | 12/2003 | Yew | |
| 6,774,135 B2 | 8/2004 | Fan et al. | |
| 7,011,831 B2 | 3/2006 | Calhoun et al. | |
| 7,045,508 B2 | 5/2006 | Scaria | |
| 7,063,962 B2 | 6/2006 | Lehmbeck | |
| 7,307,068 B2 | 12/2007 | Scaria | |
| 7,312,324 B2 | 12/2007 | Souza et al. | |
| 7,423,135 B2 | 9/2008 | Estes et al. | |
| 7,446,098 B2 | 11/2008 | Fan | |
| 7,452,716 B2 | 11/2008 | Yew | |
| 7,622,485 B2 | 11/2009 | Fan et al. | |
| 7,807,618 B2 | 10/2010 | Matalon | |
| 7,851,143 B2 | 12/2010 | Kaneski et al. | |
| 7,867,484 B2 | 1/2011 | Samulski et al. | |
| 7,892,809 B2 | 2/2011 | Bowles et al. | |
| 7,910,545 B2 | 3/2011 | Meeker et al. | |
| 7,927,585 B2 | 4/2011 | Snyder | |
| 7,927,587 B2 | 4/2011 | Blazer et al. | |
| 8,500,720 B2 | 8/2013 | Keimel | |
| 8,568,709 B2 | 10/2013 | Medin et al. | |
| 8,580,249 B2 | 11/2013 | Blazar et al. | |
| 8,592,362 B2 | 11/2013 | Benjamin et al. | |
| 8,632,764 B2 | 1/2014 | Xiao et al. | |
| 8,633,221 B2 | 1/2014 | Fan et al. | |
| 8,668,907 B2 | 3/2014 | Sakuraba et al. | |
| 8,841,427 B2 | 9/2014 | Zhu | |
| 8,889,641 B2 | 11/2014 | Asokan et al. | |

(Continued)

FOREIGN PATENT DOCUMENTS

| | | |
|---|---|---|
| AU | 2003220717 A1 | 8/2003 |
| AU | 2004242550 B2 | 4/2008 |

(Continued)

OTHER PUBLICATIONS

Lee et al, Promoter-specific lentivectors for long-term,cardiac-directed therapy of Fabry disease, (2011) 57, 115-122.*
GenScript Codon Usage Frequency Table(chart) Tool, downloaded Jun. 12, 2020, pp. 1-2.*
Park J et al. "Long-term correction of globotriaosylceramide storage in Fabry mice by recombinant adeno-associated virus-mediated gene transfer", Proc Natl Acad Sci USA. 2003; 100: 3450-4.
Hurlbut GD et al. "Preexisting immunity and low expression in primates highlight translational challenges for liver-directed AAV8-mediated gene therapy", Mol Ther. 2010; 18(11): 1983-94.
Nietupski JB et al. "Systemic administration of AAV8-a-galactosidase A induces humoral tolerance in nonhuman primates despite low hepatic expression", Mol Ther. 2011; 19(11): 1999-2011.

(Continued)

*Primary Examiner* — Maria Marvich
(74) *Attorney, Agent, or Firm* — Wilson Sonsini Goodrich & Rosati

(57) ABSTRACT

There is described a nucleic acid molecule comprising a nucleotide sequence encoding for a functional α-galactosidase A protein wherein the nucleotide sequence has at least 85% identity to the sequence of SEQ ID NO. 1. Also described is a vector, host cell or transgenic animal comprising the nucleic acid molecule; and a pharmaceutical composition comprising the nucleic acid molecule or the vector. Further, the use of the nucleic acid molecule in a method of treating Fabry disease is described.

18 Claims, 9 Drawing Sheets
Specification includes a Sequence Listing.

(56) References Cited

U.S. PATENT DOCUMENTS

| | | | |
|---|---|---|---|
| 9,000,011 B2 | 4/2015 | Lockhart et al. | |
| 9,012,224 B2 | 4/2015 | Bowles et al. | |
| 9,095,584 B2 | 8/2015 | Benjamin et al. | |
| 9,169,494 B2 | 10/2015 | Hewitt et al. | |
| 9,186,419 B2 | 11/2015 | Xiao et al. | |
| 9,194,011 B2 | 11/2015 | Shulman et al. | |
| 9,265,780 B2 | 2/2016 | Fan et al. | |
| 9,283,181 B2 | 3/2016 | Calias et al. | |
| 9,289,472 B2 | 3/2016 | Jensen et al. | |
| 9,308,281 B2 | 4/2016 | Guild et al. | |
| 9,347,050 B2 | 5/2016 | Piens et al. | |
| 9,402,921 B2 | 8/2016 | Xiao et al. | |
| 9,447,433 B2 | 9/2016 | Hirsch et al. | |
| 9,592,247 B2 | 3/2017 | Kishnani et al. | |
| 9,981,021 B1 | 5/2018 | Cao et al. | |
| 2001/0031741 A1 | 10/2001 | Ziegler et al. | |
| 2001/0036454 A1 | 11/2001 | Li et al. | |
| 2002/0014242 A1 | 2/2002 | Scaria | |
| 2002/0019361 A1 | 2/2002 | Scaria | |
| 2002/0025577 A1 | 2/2002 | Goldspink | |
| 2002/0065236 A1 | 5/2002 | Yew et al. | |
| 2002/0081654 A1 | 6/2002 | Sandrin et al. | |
| 2002/0082224 A1 | 6/2002 | Jolly et al. | |
| 2002/0095135 A1 | 7/2002 | Meeker et al. | |
| 2003/0008836 A1 | 1/2003 | Goldspink | |
| 2003/0049245 A1 | 3/2003 | Mann et al. | |
| 2003/0059920 A1 | 3/2003 | Drohan et al. | |
| 2003/0064000 A1 | 4/2003 | Burgess et al. | |
| 2003/0077806 A1 | 4/2003 | Selden et al. | |
| 2003/0100526 A1 | 5/2003 | Souza et al. | |
| 2003/0113894 A1 | 6/2003 | Selden et al. | |
| 2003/0148506 A1 | 8/2003 | Kotin et al. | |
| 2003/0224477 A1 | 12/2003 | Heartlein et al. | |
| 2004/0016021 A1 | 1/2004 | Turpen et al. | |
| 2004/0023281 A1 | 2/2004 | Turpen et al. | |
| 2004/0033217 A1 | 2/2004 | Vanguri et al. | |
| 2004/0053870 A1 | 3/2004 | Yew et al. | |
| 2004/0071686 A1 | 4/2004 | Treco et al. | |
| 2004/0077003 A1 | 4/2004 | Cocks et al. | |
| 2004/0110709 A1 | 6/2004 | Li et al. | |
| 2004/0180419 A1 | 9/2004 | Fan | |
| 2004/0204379 A1 | 10/2004 | Cheng et al. | |
| 2004/0234516 A1 | 11/2004 | Garger et al. | |
| 2004/0248262 A1 | 12/2004 | Koeberl et al. | |
| 2005/0125859 A1 | 6/2005 | Garger et al. | |
| 2005/0163756 A1 | 7/2005 | During | |
| 2006/0029656 A1 | 2/2006 | O'Donnell et al. | |
| 2006/0063733 A1 | 3/2006 | Chu | |
| 2006/0153829 A1 | 7/2006 | Fan | |
| 2006/0240521 A1 | 10/2006 | Lehmbeck | |
| 2007/0178081 A1 | 8/2007 | Fan | |
| 2007/0238693 A1 | 10/2007 | Li et al. | |
| 2008/0014188 A1 | 1/2008 | Zankel et al. | |
| 2008/0038264 A1 | 2/2008 | Bodary et al. | |
| 2008/0076174 A1 | 3/2008 | Selden et al. | |
| 2008/0096808 A1 | 4/2008 | Scaria | |
| 2009/0017533 A1 | 1/2009 | Selden et al. | |
| 2009/0042283 A1 | 2/2009 | Selden et al. | |
| 2009/0117156 A1 | 5/2009 | Passini et al. | |
| 2009/0123451 A1 | 5/2009 | Dodge et al. | |
| 2009/0148906 A1 | 6/2009 | Selden et al. | |
| 2010/0062526 A1 | 3/2010 | Selden et al. | |
| 2010/0113517 A1 | 5/2010 | Palling | |
| 2010/0144008 A1 | 6/2010 | Aerts | |
| 2010/0196345 A1 | 8/2010 | Shaaltiel et al. | |
| 2010/0196401 A1 | 8/2010 | Scaria | |
| 2010/0233200 A1 | 9/2010 | Medin | |
| 2010/0291060 A1 | 11/2010 | Sturk et al. | |
| 2010/0317690 A1 | 12/2010 | Kawamura et al. | |
| 2011/0070201 A1 | 3/2011 | Shaaltiel et al. | |
| 2011/0104130 A1* | 5/2011 | Medin | C12N 9/1229 424/93.21 |
| 2011/0104727 A1 | 5/2011 | Kaneski et al. | |
| 2011/0152319 A1 | 6/2011 | Benjamin et al. | |
| 2011/0172114 A1 | 7/2011 | Bodary et al. | |
| 2011/0212529 A1 | 9/2011 | Souza et al. | |
| 2011/0213328 A1 | 9/2011 | Keimel et al. | |
| 2011/0229971 A1 | 9/2011 | Knop et al. | |
| 2012/0183502 A1 | 7/2012 | Meeker et al. | |
| 2012/0195876 A1 | 8/2012 | Reiser | |
| 2012/0207745 A1 | 8/2012 | Godfrin et al. | |
| 2012/0230974 A1 | 9/2012 | Shaaltiel et al. | |
| 2012/0252117 A1 | 10/2012 | Selden et al. | |
| 2012/0277158 A1 | 11/2012 | Castaigne et al. | |
| 2012/0283290 A1 | 11/2012 | Sitaraman | |
| 2013/0007926 A1 | 1/2013 | Daniell et al. | |
| 2013/0158239 A1 | 6/2013 | Callewaert et al. | |
| 2013/0195800 A1 | 8/2013 | Roeth et al. | |
| 2013/0211380 A1 | 8/2013 | Cabrera Aquino et al. | |
| 2013/0244331 A1 | 9/2013 | Knop et al. | |
| 2013/0295065 A1 | 11/2013 | Shulman et al. | |
| 2014/0010861 A1 | 1/2014 | Bancel et al. | |
| 2014/0017212 A1 | 1/2014 | Rebar | |
| 2014/0037612 A1 | 2/2014 | Sturk et al. | |
| 2014/0050666 A1 | 2/2014 | Calhoun et al. | |
| 2014/0093485 A1 | 4/2014 | Medin et al. | |
| 2014/0112896 A1 | 4/2014 | Rebar | |
| 2014/0178350 A1 | 6/2014 | Vitalis et al. | |
| 2014/0206753 A1* | 7/2014 | Guild | C12N 15/52 514/44 R |
| 2014/0219986 A1 | 8/2014 | Greene et al. | |
| 2014/0350089 A1 | 11/2014 | Selden et al. | |
| 2014/0356327 A9 | 12/2014 | Passini et al. | |
| 2014/0377246 A1 | 12/2014 | Tomatsu et al. | |
| 2015/0004151 A1 | 1/2015 | Jensen et al. | |
| 2015/0057340 A1 | 2/2015 | Thess et al. | |
| 2015/0079066 A1 | 3/2015 | Rousseau et al. | |
| 2015/0132368 A1 | 5/2015 | Muro Galindo et al. | |
| 2015/0151007 A1 | 6/2015 | Dodge et al. | |
| 2015/0174214 A1 | 6/2015 | Khanna et al. | |
| 2015/0174267 A1 | 6/2015 | Castaigne et al. | |
| 2015/0238474 A1 | 8/2015 | Lockhart et al. | |
| 2015/0258081 A1 | 9/2015 | Lukas et al. | |
| 2015/0306187 A1 | 10/2015 | Sturk et al. | |
| 2015/0352093 A1 | 12/2015 | Lockhart et al. | |
| 2015/0374803 A1 | 12/2015 | Wolfe | |
| 2016/0053247 A1 | 2/2016 | Shulman et al. | |
| 2016/0060656 A1 | 3/2016 | Rebar | |
| 2016/0074533 A1 | 3/2016 | Medin | |
| 2016/0083707 A1 | 3/2016 | Radin | |
| 2016/0120960 A1 | 5/2016 | Mcivor et al. | |
| 2016/0168593 A1 | 6/2016 | Cost et al. | |
| 2016/0184409 A1 | 6/2016 | Treco et al. | |
| 2016/0208285 A1 | 7/2016 | Roeth et al. | |
| 2016/0243260 A1 | 8/2016 | Blits | |
| 2016/0324839 A1 | 11/2016 | Castelli et al. | |
| 2016/0324988 A1 | 11/2016 | Atkinson et al. | |
| 2017/0051267 A1 | 2/2017 | Calhoun | |
| 2017/0130205 A1 | 5/2017 | Chiou | |
| 2017/0165316 A1 | 6/2017 | Kishnani et al. | |
| 2017/0173184 A1 | 6/2017 | Gaspar et al. | |
| 2018/0055997 A1 | 3/2018 | Aquino et al. | |
| 2018/0086807 A1 | 3/2018 | Bancel et al. | |
| 2018/0126003 A1 | 5/2018 | Hoerr | |
| 2018/0311381 A1 | 11/2018 | Bancel et al. | |

FOREIGN PATENT DOCUMENTS

| | | |
|---|---|---|
| CN | 1230220 A | 9/1999 |
| CN | 103974619 A | 8/2014 |
| EP | 970232 A2 | 1/2000 |
| EP | 1171128 B1 | 6/2003 |
| EP | 1321143 A1 | 6/2003 |
| EP | 1336411 A1 | 8/2003 |
| EP | 935651 B1 | 12/2004 |
| EP | 1319082 B1 | 11/2005 |
| EP | 1624067 A2 | 2/2006 |
| EP | 1658857 A1 | 5/2006 |
| EP | 1232276 B1 | 4/2007 |
| EP | 1820862 A2 | 8/2007 |
| EP | 1879624 A1 | 1/2008 |
| EP | 1163349 B1 | 2/2008 |
| EP | 1242602 B1 | 2/2008 |
| EP | 2017338 A1 | 1/2009 |

(56) References Cited

FOREIGN PATENT DOCUMENTS

| | | |
|---|---|---|
| EP | 1083899 B1 | 9/2009 |
| EP | 1408117 B1 | 9/2010 |
| EP | 2275559 A2 | 1/2011 |
| EP | 2287319 A1 | 2/2011 |
| EP | 2314699 A1 | 4/2011 |
| EP | 1412505 B1 | 5/2011 |
| EP | 2327775 A2 | 6/2011 |
| EP | 2186902 B1 | 5/2012 |
| EP | 1828390 B1 | 6/2012 |
| EP | 1616016 B1 | 11/2012 |
| EP | 2550359 A1 | 1/2013 |
| EP | 1325138 B1 | 7/2013 |
| EP | 2666476 A1 | 11/2013 |
| EP | 2533050 B1 | 3/2014 |
| EP | 2143420 B1 | 6/2014 |
| EP | 1589993 B1 | 12/2014 |
| EP | 2484371 B1 | 12/2014 |
| EP | 2542675 B1 | 12/2014 |
| EP | 2252313 B1 | 4/2015 |
| EP | 2332567 B1 | 4/2015 |
| EP | 2857036 A1 | 4/2015 |
| EP | 2880156 A1 | 6/2015 |
| EP | 2659904 B1 | 9/2015 |
| EP | 2946785 A1 | 11/2015 |
| EP | 2955520 A1 | 12/2015 |
| EP | 2787345 B1 | 2/2016 |
| EP | 2796457 B1 | 5/2016 |
| EP | 2865751 B1 | 9/2016 |
| EP | 3520823 A1 | 8/2019 |
| EP | 2846821 B1 | 3/2020 |
| WO | 9640954 A1 | 12/1996 |
| WO | 9849333 A2 | 11/1998 |
| WO | 9957296 A1 | 11/1999 |
| WO | WO-200149830 A2 | 7/2001 |
| WO | 0160414 A2 | 8/2001 |
| WO | WO-01/75092 A2 | 10/2001 |
| WO | WO-200197829 A2 | 12/2001 |
| WO | WO-02064799 A2 | 8/2002 |
| WO | WO-2002095006 A3 | 11/2002 |
| WO | WO-0197829 A3 | 12/2002 |
| WO | WO-02103027 A1 | 12/2002 |
| WO | WO-03072035 A2 | 9/2003 |
| WO | 03100031 A2 | 12/2003 |
| WO | WO-2004041170 A2 | 5/2004 |
| WO | WO-2004047728 A2 | 6/2004 |
| WO | WO-2004064750 A2 | 8/2004 |
| WO | 2004074450 A2 | 9/2004 |
| WO | 2004098532 A2 | 11/2004 |
| WO | WO-2004098648 A1 | 11/2004 |
| WO | WO-2005016962 A2 | 2/2005 |
| WO | 2005056026 A1 | 6/2005 |
| WO | 2005077093 A2 | 8/2005 |
| WO | 2005089462 A2 | 9/2005 |
| WO | WO-2006119458 A1 | 11/2006 |
| WO | WO-2007053565 A2 | 5/2007 |
| WO | 2007095056 A2 | 8/2007 |
| WO | 2007137072 A2 | 11/2007 |
| WO | WO-2007092563 A3 | 11/2007 |
| WO | 2008075957 A1 | 6/2008 |
| WO | WO-2008089403 A2 | 7/2008 |
| WO | 2008121826 A2 | 10/2008 |
| WO | WO-2008132743 A2 | 11/2008 |
| WO | WO-2008134628 A2 | 11/2008 |
| WO | 2008154198 A1 | 12/2008 |
| WO | 2009032171 A1 | 3/2009 |
| WO | WO-2009030481 A1 | 3/2009 |
| WO | 2009066069 A1 | 5/2009 |
| WO | WO-2007053565 A3 | 5/2009 |
| WO | 2009097129 A1 | 8/2009 |
| WO | 2010015816 A2 | 2/2010 |
| WO | WO-2010075010 A2 | 7/2010 |
| WO | 2010093784 A2 | 8/2010 |
| WO | 2011005968 A1 | 1/2011 |
| WO | 2011039634 A2 | 4/2011 |
| WO | 2011041897 A1 | 4/2011 |
| WO | 2011051346 A1 | 5/2011 |
| WO | WO-2011061736 A1 | 5/2011 |
| WO | WO-2011 088081 A1 | 7/2011 |
| WO | WO-2011163648 A1 | 12/2011 |
| WO | 2012022777 A1 | 2/2012 |
| WO | 2012042386 A2 | 4/2012 |
| WO | WO-2012075040 A2 | 6/2012 |
| WO | 2012098537 A1 | 7/2012 |
| WO | 2012125402 A2 | 9/2012 |
| WO | WO-2012135857 A1 | 10/2012 |
| WO | WO-2012170930 A1 | 12/2012 |
| WO | 2013091897 A1 | 6/2013 |
| WO | 2013120629 A1 | 8/2013 |
| WO | 2013119880 A9 | 10/2013 |
| WO | 2013156552 A1 | 10/2013 |
| WO | WO-2013149140 A1 | 10/2013 |
| WO | WO-2013151666 A2 | 10/2013 |
| WO | WO-2013166378 A1 | 11/2013 |
| WO | 2013181454 A1 | 12/2013 |
| WO | 2014011237 A1 | 1/2014 |
| WO | 2014014938 A1 | 1/2014 |
| WO | 2014016580 A1 | 1/2014 |
| WO | 2014017915 A2 | 1/2014 |
| WO | 2014022515 A1 | 2/2014 |
| WO | WO-2014089486 A1 | 6/2014 |
| WO | 2014120900 A1 | 8/2014 |
| WO | WO-2014143701 A1 | 9/2014 |
| WO | WO-2014143734 A2 | 9/2014 |
| WO | WO-2014143932 A1 | 9/2014 |
| WO | WO-2014152513 A1 | 9/2014 |
| WO | WO-2014160092 A1 | 10/2014 |
| WO | 2014186579 A1 | 11/2014 |
| WO | WO-2014186579 A1 | 11/2014 |
| WO | WO-2014201252 A2 | 12/2014 |
| WO | 2015012924 A2 | 1/2015 |
| WO | WO-2015013148 A2 | 1/2015 |
| WO | WO-2015023796 A2 | 2/2015 |
| WO | 2015060722 A2 | 4/2015 |
| WO | 2015061464 A2 | 4/2015 |
| WO | WO-2015060722 A1 | 4/2015 |
| WO | 2015073988 A1 | 5/2015 |
| WO | 2015089067 A1 | 6/2015 |
| WO | WO-2015023796 A2 | 6/2015 |
| WO | 2015097088 A1 | 7/2015 |
| WO | 2015119989 A1 | 8/2015 |
| WO | 2015168666 A2 | 11/2015 |
| WO | WO-2015182792 A1 | 12/2015 |
| WO | 2016037162 A1 | 3/2016 |
| WO | 2016037163 A1 | 3/2016 |
| WO | 2016077356 A2 | 5/2016 |
| WO | WO-2016091391 A1 | 6/2016 |
| WO | WO-2016105889 A1 | 6/2016 |
| WO | WO-2016107877 A1 | 7/2016 |
| WO | WO-2016115382 A1 | 7/2016 |
| WO | WO-2016118780 A1 | 7/2016 |
| WO | 2016130591 A2 | 8/2016 |
| WO | WO-2016134213 A2 | 8/2016 |
| WO | WO-2016134338 A1 | 8/2016 |
| WO | 2016146760 A1 | 9/2016 |
| WO | 2016154313 A1 | 9/2016 |
| WO | 2016154344 A1 | 9/2016 |
| WO | WO-2016172155 A1 | 10/2016 |
| WO | 2016181122 A1 | 11/2016 |
| WO | 2016187017 A1 | 11/2016 |
| WO | 2016197121 A1 | 12/2016 |
| WO | 2017003792 A1 | 1/2017 |
| WO | 2017024137 A1 | 2/2017 |
| WO | 2017049161 A1 | 3/2017 |
| WO | 2017103612 A1 | 6/2017 |
| WO | 2017106236 A1 | 6/2017 |
| WO | WO-2017100467 A2 | 6/2017 |
| WO | WO-2017112733 A1 | 6/2017 |
| WO | 2017122093 A1 | 7/2017 |
| WO | WO-2017120222 A1 | 7/2017 |
| WO | WO-2017131496 A1 | 8/2017 |

(56) References Cited

FOREIGN PATENT DOCUMENTS

| WO | WO-2017136202 A1 | 8/2017 |
|---|---|---|
| WO | WO-2017191274 A2 | 11/2017 |

OTHER PUBLICATIONS

Berns KI. "Parvoviridae: The Viruses and Their Replication", Chapter 69 in Fields Virology (3rd Ed. 1996), pp. 2173-2197.
Okuyama T et al. "Liver-directed gene therapy: a retroviral vector with a complete LTR and the ApoE enhancer-enhancer-alpha 1-antitrypsin promoter dramatically increases expression of human alpha 1-antitrypsin in vivo", Human Gene Therapy. Mar. 1996; 7(5): 637-45.
Daitx et al., Comparison between alpha-galactosidase A activity in blood samples collected on filter paper, leukocytes and plasma, Clin. Biochem. 45(15):1233-8 (2012).
Lee, et al., "Promoter-specific lentivectors for long-term, cardiac-directed therapy of Fabry disease", Journal of Cardiology, (2011) 57, pp. 115-122.
Bantel-Schaal et al. "Human Adeno-Associated Virus Type 5 Is Only Distantly Related to Other Known Primate Helper-Dependent Parvoviruses", Journal of Virology. 1999; 73(2): 939-947.
Camiolo S et al. "The Relation of Codon Bias to Tissue-Specific Gene Expression in *Arabidopsis thaliana*", Genetics. 2012, vol. 192, 641-649.
Chiorini JA et al. "Cloning of adeno-associated virus type 4 (AAV4) and generation of recombinant AAV4 particles", Journal of Virology. 1997; 71, 6823-6833.
Chiorini JA et al. "Cloning and characterization of adeno-associated virus type 5", Journal of Virology. 1999; 73, 1309-1319.
Choi JO et al. "Characterization of Fabry mice treated with recombinant adeno-associated virus 2/8-mediated gene transfer", Journal of Biomedical Science. Jan. 2010: 17:26.
Dittmar KAT et al. "Tissue-Specific Difference in Human Transfer RNA Expression", PLOS Genetics. 2006; 2(12): 2107-2115.
Jung et al. "Adeno-associated viral vector-mediated gene transfer results in long-term enzymatic and functional correction in multiple organs of Fabry mice", Proc Nat Acad Sci USA. 2001; 98(5):2676-2681.
McIntosh J et al. "Therapeutic levels of FVIII following single peripheral vein administration of rAAV vector encoding a novel human factor VIII variant", Blood. Apr. 2013; 121(17): 3335-3344.
Miao CH. "Inclusion of the Hepatic Locus Control Region, an Intron, and Untranslated Region Increases and Stabilizes Hepatic Factor IX Gene Expression in Vivo but Not in Vitro", Molecular Therapy. Jun. 2000; 1(6): 522-532.
Nathwani AC et al. "Self-complementary adeno-associated virus vectors containing a novel liver-specific human factor IX expression cassette enable highly efficient transduction of murine and nonhuman primate liver", Blood. Apr. 2006; 107(7): 2653-61.
Needleman and Wunsch "A general method applicable to the search for similarities in the amino acid sequence of two proteins", J Mol Biol. Mar. 1970; 48(3); 443-53.
Newgard et al. "Sequence analysis of the cDNA encoding human liver glycogen phosphorylase reveals tissue-specific codon usage", Proc Nat Acad Sci USA. 1986; 83(21): 8132-8136.
Ohshima T et al. "alpha-Galactosidase A deficient mice: a model of Fabry disease", PNAS. Mar. 1997; 94(6): 2540-2544.
Plotkin JB et al. "Tissue-specific codon usage and the expression of human genes", PNAS. Aug. 2004; 101(34): 12588-12591.
Ruiz De Garibay AP et al. "Gene Therapy for Fabry Disease: A Review of the Literature", BioDrugs. 2013; 27:237-46.
Rutledge EA et al. "Infections clones and vectors derived from adeno-associated virus (AAV) serotypes other tan AAV type 2", Journal of Virology. 1998; 72, 309-319.
Spencer et al. "Silent Substitutions Predictably Alter Translation Elongation Rates and Protein Folding Efficiencies", J Mol Biol. 2012; 422(3): 328-335.
Srivastava A et al "Nucleotide sequence and organization of the adeno-associated virus 2 genome", Journal of Virology. Feb. 1983; 45(2): 555-64.
Wang L et al. "Sustained correction of bleeding disorder in haemophilia B mice by gene therapy", PNAS. Mar. 1999; 96(7): 3906-3910.
Wu P et al. "Mutational analysis of the adeno-associated virus type 2 (AAV2) capsid gene and construction of AAV2 vectors with altered tropism", Journal of Virology. Sep. 2000; 74(18): 8635-47.
Ziegler RJ et al. "AAV2 Vector Harboring a Liver-Restricted Promoter Facilitates Sustained Expression of Therapeutic Levels of [alpha]-Galactosidase A and the Induction of Immune Tolerance in Fabry Mice", Molecular Therapy. Feb. 2004; 9(2): 231-240.
Ziegler RJ et al. "Correction of Enzymatic and Lysosomal Storage Defects in Fabry Mice by Adenovirus-Mediated GeneTransfer", Human Gene Therapy. Jul. 1999; 10(10): 1667-1682.
Ziegler RJ et al. "Correction of the Biochemical and Functional Deficits in Fabry Mice Following AAV8-mediated Hepatic Expression of [alpha]-galactosidase A", Molecular Therapy. Mar. 2007; 15(3): 492-500.
"Liu et al., "Pedigree Investigation of Clinicopathologic Features and Alpha-galactosidase A Gene Mutation in a Family with Fabry Disease", Journal of Sichuan University (Medical Science Edition), 2012, vol. 43 No. 6 pp. 948-951", abstract only.
"Rang et al., Preliminary Study on the Construction, Expression and Biochemical Characteristics of a Human Alpha-galactosidase A Mutant", China Masters' Theses Full-text Database, published online Jul. 15, 2012, vol. 7, pp. E069-13, abstract only.
"Miyamura, et al., A carboxy-terminal truncation of human alpha-galactosidase A in a heterozygous female with Fabry disease and modification of the enzymatic activity by the carboxy-terminal domain. Increased, reduced, or absent enzyme activity depending on number of amino acid residues deleted. J Clin Invest. 15;98(8):1809-17".
"Meghdari, et al., Carboxyl-Terminal Truncations Alter the Activity of the Human α-Galactosidase A. PLoS ONE 10(2): e0118341. doi: 10.1371/journal, pone.0118341".
"Presnyak, et al., Cell, 2015, vol. 160, No. 6, pp. 1111-1124". Codon Optimalit Is a Major Determinant of mRNX Stability.
Takahashi, et al. "Long-term systemic therapy of Fabry disease in a knockout mouse by adeno-associated virus-mediated muscle-directed gene transfer. PNAS Oct. 2002, 99 (21) 13777-13782; DOI: 10.1073/pnas.222221899".

\* cited by examiner

SEQUENCE LISTING

```
<160> NUMBER OF SEQ ID NOS: 3

<210> SEQ ID NO 1
<211> LENGTH: 1290
<212> TYPE: DNA
<213> ORGANISM: Artificial sequence
<220> FEATURE:
<223> OTHER INFORMATION: nucleotide sequence of codon optimised
      alpha-galactosidase A

<400> SEQUENCE: 1
atgcagctgc ggaaccccga actgcacctg ggatgcgccc tggcactgag atttctggca      60
ctggtctctt gggatattcc tggagcaagg gccctggaca acggactggc tcgaaccccc     120
acaatgggct ggctgcactg ggagaggttc atgtgcaatc tggactgtca ggaggaacct     180
gatagctgca tctccgaaaa gctgtttatg gagatggccg aactgatggt gtctgagggc     240
tggaaagatg ctgggtacga atatctgtgc attgacgatt gttggatggc accacagcga     300
gacagtgagg gccggctgca ggcagatcca cagagattcc ctcacgggat caggcagctg     360
gccaactacg tgcatagcaa ggggctgaaa ctgggaatct acgcagacgt gggcaataag     420
acatgtgccg gcttccccgg gtcctttgga tactatgaca tcgatgcaca gactttcgcc     480
gactggggcg tggatctgct gaagtttgac ggatgctact gtgatagtct ggagaacctg     540
gctgatggat ataaacacat gtcactggca ctgaatagga ccggccgcag catcgtctac     600
```

```
tcctgcgagt ggcccctgta tatgtggcca ttccagaagc ccaactacac agaaatccgc    660
cagtattgta accattggcg aaattttgct gacattgacg attcttggaa gagtatcaaa    720
tcaattctgg actggactag cttcaaccag gaacgaatcg tggatgtcgc aggacctggc    780
gggtggaatg acccagatat gctggtcatc ggcaacttcg ggctgagctg aatcagcag    840 gtcacccaga tggccctgtg gctatcatg gccgctccac tgtttatgtc aaatgacctg    900
agacacatta gccccaggc aaaggccctg ctgcaggaca agatgtgat cgccattaac    960 caggaccctc tgggaaagca gggctaccag ctgcgacagg gggataattt tgaagtgtgg   1020
gaacgccctc tgtccggact ggcttgggca gtcgccatga tcaaccggca ggagattgga   1080
ggcccaagat cctacacaat cgctgtggca tctctgggga aggagtcgc ttgcaatccc    1140 gcatgtttca ttactcagct gctgcctgtg aagcgcaaac tgggctttta tgaatggacc   1200
tctcggctga aagtcatat caacccaact ggcactgtcc tgctgcagct ggagaacact   1260
atgcagatga gcctgaaaga cctgctgtaa                                    1290

<210> SEQ ID NO 2
<211> LENGTH: 335
<212> TYPE: DNA
<213> ORGANISM: Artificial sequence
<220> FEATURE:
<223> OTHER INFORMATION: nucleotide sequence of promoter HLP2

<400> SEQUENCE: 2
ccctaaaatg ggcaaacatt gcaagcagca aacagcaaac acacagccct ccctgcctgc     60
tgaccttgga gctggggcag aggtcagaca cctctctggg cccatgccac ctccaactgg    120
acacaggacg ctgtggtttc tgagccaggg ggcgactcag atcccagcca gtggacttag    180
cccctgtttg ctcctccgat aactgggtg accttggtta atattcacca gcagcctccc     240
ccgttgcccc tctggatcca ctgcttaaat acggacgagg acagggccct gtctcctcag    300
cttcaggcac caccactgac ctgggacagt gaatc                               335

<210> SEQ ID NO 3
<211> LENGTH: 2330
<212> TYPE: DNA
<213> ORGANISM: Artificial sequence
<220> FEATURE:
<223> OTHER INFORMATION: nucleotide sequence of vector construct
      including promoter and codon optimised alpha-galactosidase A
      sequence

<400> SEQUENCE: 3
gggccactcc ctctctgcgc gctcgctcgc tcactgaggc cgggcgacca aggtcgccc     60 gacgcccggg ctttgcccgg gcggcctcag tgagcgagcg agcgcgcaga gagggagtgg    120
ccaactccat cactaggggt tcctggaggg gtggagtcgt gacccctaaa atgggcaaac    180
attgcaagca gcaaacagca aacacacagc cctccctgcc tgctgacctt ggagctgggg    240
cagaggtcag agacctctct gggcccatgc cacctccaac atccactcga ccccttggaa    300
tttcggtgga gaggagcaga ggttgtcctg gcgtggttta ggtagtgtga gaggggaatg    360
actcctttcg gtaagtgcag tggaagctgt acactgccca gcaaagcgt ccgggcagcg    420 taggcgggcg actcagatcc cagccagtgg acttagcccc tgtttgctcc tccgataact    480
ggggtgacct tggttaatat tcaccagcag cctcccccgt tgcccctctg gatccactgc    540
ttaaatacgg acgaggacag ggccctgtct cctcagcttc aggcaccacc actgacctgg    600
```

```
gacagtgaat ccggactcta aggtaaatat aaaattttta agtgtataat gtgttaaact      660
actgattcta attgtttctc tcttttagat tccaaccttt ggaactgaat tcgcggccgc      720
catgcagctg cggaaccccg aactgcacct gggatgcgcc ctggcactga gatttctggc      780
actggtctct tgggatattc ctggagcaag ggccctggac aacggactgg ctcgaacccc      840
cacaatgggc tggctgcact gggagaggtt catgtgcaat ctggactgtc aggaggaacc      900
tgatagctgc atctccgaaa agctgtttat ggagatggcc gaactgatgg tgtctgaggg      960
ctggaaagat gctgggtacg aatatctgtg cattgacgat tgttggatgg caccacagcg     1020
agacagtgag ggccggctgc aggcagatcc acagagattc cctcacggga tcaggcagct     1080
ggccaactac gtgcatagca aggggctgaa actgggaatc tacgcagacg tgggcaataa     1140
gacatgtgcc ggcttccccg gtcctttgg atactatgac atcgatgcac agactttcgc      1200
cgactggggc gtggatctgc tgaagtttga cggatgctac tgtgatagtc tggagaacct     1260
ggctgatgga tataaacaca tgtcactggc actgaatagg accggccgca gcatcgtcta     1320
ctcctgcgag tggcccctgt atatgtgcc attccagaag cccaactaca cagaaatccg      1380
ccagtattgt aaccattggc gaaattttgc tgacattgac gattcttgga agagtatcaa     1440
atcaattctg gactggacta gcttcaacca ggaacgaatc gtggatgtcg caggacctgg     1500
cgggtggaat gacccagata tgctggtcat cggcaacttc gggctgagct ggaatcagca     1560
ggtcacccag atggccctgt gggctatcat ggccgctcca ctgtttatgt caaatgacct     1620
gagacacatt agcccccagg caaaggccct gctgcaggac aaagatgtga tcgccattaa     1680 ccaggacct ctgggaaagc agggctacca gctgcgacag ggggataatt ttgaagtgtg      1740
ggaacgccct ctgtccggac tggcttgggc agtcgccatg atcaaccggc aggagattgg     1800
aggcccaaga tcctacacaa tcgctgtggc atctctgggg aaaggagtcg cttgcaatcc     1860
cgcatgtttc attactcagc tgctgcctgt gaagcgcaaa ctgggctttt atgaatggac     1920
ctctcggctg agaagtcata tcaacccaac tggcactgtc ctgctgcagc tggagaacac     1980
tatgcagatg agcctgaaag acctgctgta agatatctga tcatgactcg atgctttatt     2040
tgtgaaattt gtgatgctat tgctttattt gtaaccatta taagctgcaa taaacaagtt     2100
aacaacaaca attgcattca ttttatgttt caggttcagg gggaggtgtg ggaggttttt     2160
taaactagtc cactccctct ctgcgcgctc gctcgctcac tgaggccggg cgaccaaagg     2220
tcgcccgacg cccgggcttt gcccgggcgg cctcagtgag cgagcgagcg cgcagagagg     2280
gacagatccg ggcccgcatg cgtcgacaat tcactggccg tcgttttaca               2330
```

FABRY DISEASE GENE THERAPY

CROSS-REFERENCE TO RELATED APPLICATIONS

This application is a national phase entry under 35 U.S.C. § 371 of International Patent Application PCT/GB2016/051328, filed May 10, 2016, designating the United States of America and published in English as International Patent Publication WO 2016/181122 A1 on Nov. 17, 2016, which claims the benefit under Article 8 of the Patent Cooperation Treaty to Great Britain Patent Application Serial No. 1508025.2 filed May 11, 2015.

STATEMENT ACCORDING TO 37 C.F.R. § 1.821(c) or (e) -SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

FIELD OF THE INVENTION

The invention relates to a new gene therapy approach for treating Fabry disease.

BACKGROUND TO THE INVENTION

Fabry disease is a rare X-linked inherited multisystem lysosomal storage disorder, with an estimated prevalence of approximately 1:40,000. It is caused by a deficiency of the α-galactosidase A enzyme resulting in the accumulation of neutral glycosphingolipids in the lysosomes of a variety of organs including the endothelial and smooth muscle cells of blood vessels. This accumulation leads to an impairment of organ function leading to end stage renal disease, cardiac complications and stroke, associated with a reduced life expectancy of approximately 58 years.

Haematopoietic stem cell transplantation has demonstrated clinical benefit in Fabry disease but is associated with high morbidity and mortality. In 2002, the European Medicines Agency approved two recombinant enzymes: agalsidase alfa (Shire HGT, Boston Mass., USA) and agalsidase beta (Genzyme Inc, Boston Mass., USA), which represent the only currently available specific treatment for Fabry disease. Enzyme replacement therapy (ERT) is a reasonable and promising approach for the treatment of Fabry disease but does not represent a cure, requiring weekly intravenous administration for the life-time of the patients at an estimated cost to the NHS of approximately £200K/year. Additionally a significant proportion of patients (55-88%) develop neutralising antibodies to the α-galactosidase A, thus rendering ERT ineffective.

In contrast, gene therapy for Fabry disease offers the potential for a cure through persistent, endogenous production of α-galactosidase A following the transfer of a normal copy of the α-galactosidase A gene to an affected patient.

The inventors have developed a gene therapy approach using adeno-associated viral vectors (AAV) to mediate transfer and expression of the α-galactosidase A gene. As Fabry disease arises from a defect in a single gene, relatively low levels of enzyme correction will reduce storage of glycosphingolipids. Additionally, correction of a small number of cells will potentially correct distant cells too as a result of metabolic cross-correction mechanisms, wherein corrected cells secrete α-galactosidase A that can correct bystander cells. Finally, the inventor's approach entails liver mediated expression of α-galactosidase A following in-vivo, AAV mediated gene transfer of hepatocytes, which results in tolerance to the transgenic protein, thereby reducing the risk of developing neutralising antibodies to α-galactosidase A.

SUMMARY OF THE INVENTION

In a first aspect of the invention, there is provided a nucleic acid molecule comprising a nucleotide sequence encoding for a functional α-galactosidase A protein wherein the nucleotide sequence has at least 85% identity to the sequence of SEQ ID NO. 1.

The inventors have surprisingly found that the novel codon optimised sequence of SEQ ID NO. 1 results in increased expression of the α-galactosidase A protein in hepatocytes transduced with an AAV vector under the control of a liver specific promoter, versus an identical construct containing the wild-type α-galactosidase A cDNA.

The nucleotide sequence has at least 85% identity to the sequence of SEQ ID NO. 1. In some embodiments, the nucleotide sequence has at least 86% identity to the sequence of SEQ ID NO. 1. In other embodiments, the nucleotide sequence has at least 87% identity to the sequence of SEQ ID NO. 1. In particular embodiments, the nucleotide sequence has at least 88% identity to the sequence of SEQ ID NO. 1. In further embodiments, the nucleotide sequence has at least 89% identity to the sequence of SEQ ID NO. 1. In some embodiments, the nucleotide sequence has at least 90% identity to the sequence of SEQ ID NO. 1. In other embodiments, the nucleotide sequence has at least 91% identity to the sequence of SEQ ID NO. 1. In particular embodiments, the nucleotide sequence has at least 92% identity to the sequence of SEQ ID NO. 1. In further embodiments, the nucleotide sequence has at least 93% identity to the sequence of SEQ ID NO. 1. In some embodiments, the nucleotide sequence has at least 94% identity to the sequence of SEQ ID NO. 1. In other embodiments, the nucleotide sequence has at least 95% identity to the sequence of SEQ ID NO. 1. In particular embodiments, the nucleotide sequence has at least 96% identity to the sequence of SEQ ID NO. 1. In further embodiments, the nucleotide sequence has at least 97% identity to the sequence of SEQ ID NO. 1. In some embodiments, the nucleotide sequence has at least 98% identity to the sequence of SEQ ID NO. 1. In other embodiments, the nucleotide sequence has at least 99% identity to the sequence of SEQ ID NO. 1. In particular embodiments, the nucleotide sequence has the sequence of SEQ ID NO. 1.

The nucleotide sequence encodes for a functional α-galactosidase A protein. A functional α-galactosidase A protein hydrolyses the terminal alpha-galactosyl moieties from glycolipids and glycoproteins. Suitable methods for assaying for α-galactosidase A activity are well known to those skilled in the art. Preferably, the nucleotide sequence encodes for α-galactosidase A protein having the wild type amino acid sequence. This sequence is well known to those skilled in the art. For example, this information can be found on GenBank (http://www.ncbi.nlm.nih.gov/genbank) under accession number CAA29232.1 (GI: 757912). Further information on this protein can be found under NCBI Reference Sequence: NP 000160.1 (GI: 4504009). The wild type protein sequence has 429 amino acids.

In a second aspect of the invention there is provided a vector for expressing α-galactosidase A protein.

The vector comprises the nucleic acid molecule described above. This means that the vector contains a nucleotide sequence encoding for a functional α-galactosidase A protein so that when this sequence is expressed, a functional α-galactosidase A protein is produced by the cell in which the vector is contained.

The sequence of SEQ ID NO. 1 is a codon optimised α-galactosidase A nucleotide sequence. This sequence has not been codon optimised in a normal way. Instead, the codons have been selected based on the codons used for proteins which are expressed at a high level in the liver. The reason for this is that the vector is normally expressed in the liver. This special codon optimisation process has been found to produce a nucleotide sequence which gives surprisingly high expression.

The nucleotide sequence encoding for a α-galactosidase A protein is preferably between 1265 and 1315 nucleotides in length. In some embodiments, the nucleotide sequence encoding for a functional α-galactosidase A protein is between 1270 and 1310 nucleotides in length. In other embodiments, the nucleotide sequence encoding for a functional α-galactosidase A protein is between 1275 and 1305 nucleotides in length. In particular embodiments, the nucleotide sequence encoding for a functional α-galactosidase A protein is between 1280 and 1300 nucleotides in length.

Preferably the vector further comprises a promoter. The promoter causes expression of the nucleotide sequence encoding for a functional α-galactosidase A protein. Any appropriate promoter may be used, such as HLP, LP1, HCR-hAAT, ApoE-hAAT, and LSP. These promoters are described in more detail in the following references: HLP: McIntosh J. et al., Blood 2013 Apr. 25, 121(17):3335-44; LP1: Nathwani et al., Blood. 2006 Apr. 1, 107(7): 2653-2661; HCR-hAAT: Miao et al., Mol Ther. 2000; 1: 522-532; ApoE-hAAT: Okuyama et al., Human Gene Therapy, 7, 637-645 (1996); and LSP: Wang et al., Proc Natl Acad Sci USA. 1999 Mar. 30, 96(7): 3906-3910. A preferred promoter is also described in WO 2011/005968. Another preferred promoter has the sequence of SEQ ID NO. 2 and is referred to as HLP2. The promoter having SEQ ID NO. 2 is a liver specific promoter which has been found to give particularly good expression in the liver. Whilst giving good expression, this promoter is also relatively small which allows more efficient packaging of the vector. Preferably, the promoter is a liver specific promoter.

SEQ ID NO. 3 is the nucleotide sequence of a vector construct including a promoter and a nucleotide sequence encoding for a functional α-galactosidase A protein. Therefore, the nucleic acid molecule of the invention may comprise a nucleotide sequence having at least 90% identity to the sequence of SEQ ID NO. 3. In other embodiments, the nucleotide sequence has at least 91% identity to the sequence of SEQ ID NO. 3. In particular embodiments, the nucleotide sequence has at least 92% identity to the sequence of SEQ ID NO. 3. In further embodiments, the nucleotide sequence has at least 93% identity to the sequence of SEQ ID NO. 3. In some embodiments, the nucleotide sequence has at least 94% identity to the sequence of SEQ ID NO. 3. In other embodiments, the nucleotide sequence has at least 95% identity to the sequence of SEQ ID NO. 3. In particular embodiments, the nucleotide sequence has at least 96% identity to the sequence of SEQ ID NO. 3. In further embodiments, the nucleotide sequence has at least 97% identity to the sequence of SEQ ID NO. 3. In some embodiments, the nucleotide sequence has at least 98% identity to the sequence of SEQ ID NO. 3. In other embodiments, the nucleotide sequence has at least 99% identity to the sequence of SEQ ID NO. 3. In particular embodiments, the nucleotide sequence has the sequence of SEQ ID NO. 3.

The vector may be any appropriate vector for expressing the α-galactosidase A protein, including viral and non-viral vectors. Viral vectors include a parvovirus, an adenovirus, a retrovirus, a lentivirus or a herpes simplex virus. The parvovirus may be an adenovirus-associated virus (AAV). The vector is preferably a recombinant adeno-associated viral (rAAV) vector or a lentiviral vector. More preferably, the vector is a rAAV vector.

A vector according to the invention may be a gene delivery vector. Such a gene delivery vector may be a viral gene delivery vector or a non-viral gene delivery vector.

Accordingly, the present invention provides gene delivery vectors based on animal parvoviruses, in particular dependoviruses such as infectious human or simian AAV, and the components thereof (e.g., an animal parvovirus genome) for use as vectors for introduction and/or expression of an α-galactosidase A protein in a mammalian cell. The term "parvoviral" as used herein thus encompasses dependoviruses such as any type of AAV.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture. The genus Dependovirus includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience, the present invention is further exemplified and described herein by reference to AAV. It is, however, understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild type (wt) AAV infection in mammalian cells the Rep genes (i.e. encoding Rep78 and Rep52 proteins) are expressed from the P5 promoter and the P19 promoter, respectively, and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

In an AAV suitable for use as a gene therapy vector, the vector genome typically comprises a nucleic acid to be packaged for delivery to a target cell. According to this particular embodiment, the heterologous nucleotide sequence is located between the viral ITRs at either end of the vector genome. In further preferred embodiments, the parvovirus (e.g. AAV) cap genes and parvovirus (e.g. AAV) rep genes are deleted from the template genome (and thus from the virion DNA produced therefrom). This configuration maximizes the size of the nucleic acid sequence(s) that can be carried by the parvovirus capsid.

According to this particular embodiment, the nucleic acid is located between the viral ITRs at either end of the substrate. It is possible for a parvoviral genome to function with only one ITR. Thus, in a gene therapy vector of the invention based on a parvovirus, the vector genome is flanked by at least one ITR, but, more typically, by two AAV ITRs (generally with one either side of the vector genome, i.e. one at the 5' end and one at the 3' end). There may be intervening sequences between the nucleic acid in the vector genome and one or more of the ITRs.

Preferably, the nucleotide sequence encoding a functional α-galactosidase A protein (for expression in the mammalian cell) will be incorporated into a parvoviral genome located between two regular ITRs or located on either side of an ITR engineered with two D regions.

AAV sequences that may be used in the present invention for the production of AAV gene therapy vectors can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chiorini et al, 1997; Srivastava et al, 1983; Chiorini et al, 1999; Rutledge et al, 1998; and Wu et al, 2000. AAV serotype 1, 2, 3, 4, 5, 6, 7, 8 or 9 may be used in the present invention. However, AAV serotypes 1, 5 or 8 are preferred sources of AAV sequences for use in the context of the present invention. The sequences from the AAV serotypes may be mutated or engineered when being used in the production of gene therapy vectors.

Preferably, the AAV ITR sequences for use in the context of the present invention are derived from AAV1, AAV2, AAV4 and/or AAV6. Likewise, the Rep (Rep78 and Rep52) coding sequences are preferably derived from AAV1, AAV2, AAV4 and/or AAV6. The sequences coding for the VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g. capsid shuffling techniques and AAV capsid libraries.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al, 1999). Moreover, the Rep sequences and ITRs of many AAV serotypes are known to efficiently cross-complement (i.e., functionally substitute) corresponding sequences from other serotypes in production of AAV particles in mammalian cells. US 2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped AAV particles comprising the capsid proteins of a serotype (e.g., AAV1, 5 or 8) and the Rep and/or ITR sequences of another AAV serotype (e.g., AAV2). Such pseudotyped rAAV particles are a part of the present invention.

Modified "AAV" sequences also can be used in the context of the present invention, e.g. for the production of AAV gene therapy vectors. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e. a nucleotide sequence comprises an AAV5 Rep78). Such ITR and Rep sequences can be modified as desired to obtain efficient production of AAV5 or pseudotyped AAV5 vectors. For example, the start codon of the Rep sequences can be modified, VP splice sites can be modified or eliminated, and/or the VP1 start codon and nearby nucleotides can be modified to improve the production of AAV5 vectors.

Thus, the viral capsid used in the invention may be from any parvovirus, either an autonomous parvovirus or dependovirus, as described above. Preferably, the viral capsid is an AAV capsid (e. g., AAV1, AAV2, AAV3, AAV4, AAV5 or AAV6 capsid). In general, the AAV1 capsid or AAV6 capsid are preferred. The choice of parvovirus capsid may be based on a number of considerations as known in the art, e.g., the target cell type, the desired level of expression, the nature of the heterologous nucleotide sequence to be expressed, issues related to viral production, and the like. For example, the AAV1 and AAV6 capsid may be advantageously employed for skeletal muscle; AAV1, AAV5 and AAV8 for the liver and cells of the central nervous system (e.g., brain); AAV5 for cells in the airway and lung or brain; AAV3 for bone marrow cells; and AAV4 for particular cells in the brain (e. g., appendable cells).

It is within the technical skills of the skilled person to select the most appropriate virus, virus subtype or virus serotype. Some subtypes or serotypes may be more appropriate than others for a certain type of tissue.

For example, liver-specific expression of a nucleic acid of the invention may advantageously be induced by AAV-mediated transduction of liver cells. Liver is amenable to AAV-mediated transduction, and different serotypes may be used (for example, AAV1, AAV5 or AAV8). Transduction of muscle may be accomplished by administration of an AAV encoding a nucleic acid via the blood stream. Thus, intravenous or intra-arterial administration is applicable.

A parvovirus gene therapy vector prepared according to the invention may be a "hybrid" particle in which the viral TRs and viral capsid are from different parvoviruses. Preferably, the viral TRs and capsid are from different serotypes of AAV. Likewise, the parvovirus may have a "chimeric" capsid (e. g., containing sequences from different parvoviruses, preferably different AAV serotypes) or a "targeted" capsid (e. g., a directed tropism).

In the context of the invention "at least one parvoviral ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans-acting replication proteins such as e.g. Rep 78 (or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. A parvovirus replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nucleotide sequence can be used in the context of the present invention. Preferably, however, two or another even number of regular ITRs are used. Most preferably, two ITR sequences are used. A preferred parvoviral ITR is an AAV ITR. For safety reasons it may be desirable to construct a parvoviral (AAV) vector that is unable to further propagate after initial introduction into a cell. Such a safety mechanism for limiting undesirable vector propagation in a recipient may be provided by using AAV with a chimeric ITR as described in US 2003148506.

Those skilled in the art will appreciate that the viral Rep protein(s) used for producing an AAV vector of the invention may be selected with consideration for the source of the viral ITRs. For example, the AAV5 ITR typically interacts more efficiently with the AAV5 Rep protein, although it is not necessary that the serotype of ITR and Rep protein(s) are matched.

The ITR(s) used in the invention are typically functional, i.e. they may be fully resolvable and are preferably AAV sequences, with serotypes 1, 2, 3, 4, 5 or 6 being preferred. Resolvable AAV ITRs according to the present invention need not have a wild-type ITR sequence (e. g., a wild-type sequence may be altered by insertion, deletion, truncation or missense mutations), as long as the ITR mediates the desired functions, e. g., virus packaging, integration, and/or provirus rescue, and the like.

Advantageously, by using a gene therapy vector as compared with previous approaches, the restoration of protein synthesis, i.e. α-galactosidase A synthesis, is a characteristic that the transduced cells acquire permanently or for a sustained period of time, thus avoiding the need for continuous administration to achieve a therapeutic effect.

Accordingly, the vectors of the invention therefore represent a tool for the development of strategies for the in vivo delivery of an α-galactosidase A nucleotide sequence, by engineering the nucleic acid within a gene therapy vector that efficiently transduces an appropriate cell type, such as a liver cell.

The vector may be a single stranded vector or a self-complementary vector. In some embodiments, the vector is a single stranded vector. In other embodiments, the vector is a self-complementary vector.

The vector may further comprise a poly A tail. Preferably, this is positioned downstream of the nucleotide sequence encoding for a functional α-galactosidase A protein. Preferably, the poly A tail is a bovine growth hormone poly A tail. Preferably, this is between 250 and 270 nucleotides in length.

The vector may comprise other elements to allow the functional α-galactosidase A protein to be expressed. Such elements are well known to a person skilled in the art.

Preferably, the nucleic acids described above are isolated.

It would be well with the capabilities of a skilled person to produce the nucleic acid molecules described above. This could be done, for example, using chemical synthesis of a given sequence.

Further, a skilled person would readily be able to determine whether a nucleic acid expresses a functional protein. Suitable methods would be apparent to those skilled in the art. For example, one suitable in vitro method involves inserting the nucleic acid into a vector, such as a lentiviral or an AAV vector, transducing host cells, such as 293T or HeLa cells, with the vector, and assaying for α-galactosidase A activity. Alternatively, a suitable in vivo method involves transducing a vector containing the nucleic acid into mice with Fabry disease and assaying for functional α-galactosidase A in the plasma of the mice. Suitable methods are described in more detail below.

The nucleic acid can be any type of nucleic acid composed of nucleotides. The nucleic acid should be able to be expressed so that a protein is produced. Preferably, the nucleic acid is DNA or RNA.

The invention also provides a host cell comprising any one of the nucleic acid molecules or vectors described above. Preferably, the vector is capable of expressing the α-galactosidase A nucleotide sequence in the host. The host may be any suitable host.

As used herein, the term "host" refers to organisms and/or cells which harbour a nucleic acid molecule or a vector of the invention, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host. A host cell may be in the form of a single cell, a population of similar or different cells, for example in the form of a culture (such as a liquid culture or a culture on a solid substrate), an organism or part thereof.

A host cell according to the invention may permit the expression of a nucleic acid molecule of the invention. Thus, the host cell may be, for example, a bacterial, a yeast, an insect or a mammalian cell.

In addition, the invention provides a transgenic animal comprising cells comprising the nucleic acid molecule encoding for a functional α-galactosidase A protein described above or a vector described above. Preferably the animal is a non-human mammal, especially a primate. Alternatively, the animal may be a rodent, especially a mouse; or may be canine, feline, ovine or porcine.

In one aspect, the invention provides a pharmaceutical composition comprising a nucleic acid molecule or a vector of the invention and one or more pharmaceutically acceptable excipients. The one or more excipients include carriers, diluents and/or other medicinal agents, pharmaceutical agents or adjuvants, etc.

The invention also provides a method of treating Fabry disease comprising administering a therapeutically effective amount of a vector as described above to a patient suffering from Fabry disease. Preferably, the patient is human.

When Fabry disease is "treated" in the above method, this means that one or more symptoms of Fabry disease are ameliorated. It does not mean that the symptoms of Fabry disease are completely remedied so that they are no longer present in the patient, although in some methods, this may be the case. The method of treating results in one or more of the symptoms of Fabry disease being less severe than before treatment.

A "therapeutically effective amount" refers to an amount effective, at dosages and for periods of time necessary, to achieve the desired therapeutic result, such as raising the level of functional α-galactosidase A in a subject (so as to lead to functional α-galactosidase A production to a level sufficient to ameliorate the symptoms of Fabry disease).

Delivery of a nucleic acid or vector of the invention to a host cell in vivo may result in an increase of functional α-galactosidase A in the host, for example to a level that ameliorates one or more symptoms of Fabry disease.

The level of naturally occurring α-galactosidase A in a subject suffering from Fabry disease varies depending on the severity of the Fabry disease. Patients with a severe form of the disease have α-galactosidase A levels of less than about 1% of the level found in a normal healthy subject (referred to herein as "a normal level"). It has been found that when the method of treatment of the invention is used, it can cause an increase in the level of functional α-galactosidase A to at least about 1% of normal levels. In some embodiments, the method of treatment of the invention causes an increase in the level of functional α-galactosidase A to at least about 2%, at least about 3%, at least about 4%, at least about 10%, at least about 15%, at least about 20% or at least about 25% of normal levels. In a particular embodiment, the method of treatment of the invention causes an increase in the level of functional α-galactosidase A to at least about 30% of normal levels.

In one embodiment, the method of treatment of the invention causes an increase in the level of functional α-galactosidase A to, at most, normal levels.

The activity of functional α-galactosidase A can be measured relatively easily and methods for measuring α-galactosidase A activity are well known to those skilled in the art. The activity of α-galactosidase can conveniently be measured in blood using a blood spot as described in Clin. Biochem. 45(15):1233-8 (2012). The principle of this method is that at acidic pH, α-galactosidase hydrolyses the substrate, 4-methylumbelliferyl-a-D-galactopyranoside, to 4-methylumbelliferone and galactose. Adding alkaline buffer stops the enzyme reaction and causes the 4-methylumbelliferone to fluoresce at a different wavelength from the unhydrolysed substrate, thereby permitting its measurement in the presence of a vast excess of unhydrolysed substrate. In leucocytes usually over 95% of the total α-galactosidase activity is α-galactosidase A whereas in plasma and cultured cells, the isoenzyme, α-galactosidase B can significantly contribute to the total α-galactosidase activity. α-galactosidase A can be measured in the presence of α-galactosidase B by making use of the increased heat liability of the A isoenzyme and in plasma the α-galactosidase B can be inhibited by the addition of a-NAc galactosamine. A key advantage of this method is that only 5 ul spot of dried whole blood on filter paper is required. This offers the advantage of measuring α-galactosidase levels in real time as the experiment in Fabry Ko mouse proceeds following vector administration.

Alternatively, α-galactosidase A activity in plasma can be assessed on a terminal bleed in mice following gene transfer. This method is based on the fact that at acidic pH, α-galactosidase hydrolyses the substrate, 4-methylumbelliferyl-a-D-galactopyranoside, to 4-methylumbelliferone and galactose, as above. In addition, α-galactosidase can also be measured using standard Western blot assay or standard (ELISA type) immunoassays which show antigen levels.

Further, the invention provides the nucleic acid molecule encoding for a functional α-galactosidase A protein as described above, or a vector as described above for use in therapy, for example, in the treatment of Fabry disease.

In addition, the invention provides the use of the nucleic acid molecule encoding for a functional α-galactosidase A protein as described above or a vector as described above in the manufacture of a medicament for treating Fabry disease.

The invention also provides a method for delivery of a nucleotide sequence encoding a functional α-galactosidase A protein to a subject, which method comprises administering to the said subject a nucleic acid molecule encoding a functional α-galactosidase A protein as described above or a vector as described above.

In the description above, the term "identity" is used to refer to the similarity of two sequences. For the purpose of this invention, it is defined here that in order to determine the percent identity of two nucleotide sequences, the sequences are aligned for optimal comparison purposes (e.g., gaps can be introduced in the sequence of a first nucleic acid for optimal alignment with a second amino or nucleic acid sequence). The nucleotide residues at nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, about twenty, about fifty, about one hundred, about two hundred, about five hundred, about 1000 or about 2000 or more contiguous nucleic acid residues.

The skilled person will be aware of the fact that several different computer programs are available to determine the homology or identity between two sequences. In preferred embodiments, the identity between two sequences is analysed using the software package Clone Manager Professional version 9 (preferably, version 9.4). This analysis tool is produced by Sci-Ed Software (Scientific & Educational Software, 11010 Lake Grove Blvd, Ste 100, PMB 122, Morrisville, N.C. 27560, USA—http://www.scied.com/index.htm). The settings used to compare the sequences are preferably as follows: alignment: Global DNA alignment; parameters: both strands; scoring matrix: linear (mismatch 2, OpenGap 4, ExtGap 1). Alternatively the following methods such as Fast Scan-MaxScore and Fast Scan MaxQual can also be used with the same software using the local settings.

Other methods can also be used to determine sequence identity. For example, the percent identity between two amino acid or nucleic acid sequences can be determined using the Needleman and Wunsch (1970) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6.

All patent and literature references cited in the present specification are hereby incorporated by reference in their entirety.

A skilled person will appreciate that all aspects of the invention, whether they relate to, for example, the nucleic acid, the vector, the host cell or the use, are equally applicable to all other aspects of the invention. In particular, aspects of the method of treatment, for example, the administration of the nucleic acid or vector, may have been described in greater detail than in some of the other aspects of the invention, for example, relating to the use of the nucleic acid or vector for treating Fabry disease. However, the skilled person will appreciate where more detailed information has been given for a particular aspect of the invention, this information is generally equally applicable to other aspects of the invention. Further, the skilled person will also appreciate that the description relating to the method of treatment is equally applicable to the use of the nucleic acid or vector in treating Fabry disease.

DETAILED DESCRIPTION OF THE INVENTION

The invention will now be described in detail by way of example only with reference to the figures in which:

FIG. 1 shows an alkaline gel analysis illustrating that scAAV8 vectors expressing wildtype (wt) α-galactosidase A (left lane beside ladder) and codon optimised (codop) α-galactosidase A (right lane) are both fully packaged, with no detectable partial genomes. These vectors were pseudotyped with serotype 8 capsid in which the wt or codon optimised α-galactosidase A gene was under the control of a liver specific HLP promoter.

FIG. 2 illustrates that a scAAV vector comprising codon optimised α-galactosidase A (scAAV-GLA-codop), when transduced into HUH7 liver carcinoma cells at a Multiplicity of Infection (MOI) of $1 \times 10^7$ vg/cell, does not affect endogenous levels of α-galactosidase A transcript (top left panel) but expresses high levels of codon-optimised α-galactosidase A mRNA (top right panel). scAAV-GLA-codop was transduced into HUH7 cells at increasing MOIs, leading to increasing and dose-specific expression of α-galactosidase A transcript (bottom panel).

FIG. 3 illustrates that scAAV vectors expressing wild type (WT-GLA) and codon-optimised (codop-GLA) α-galactosidase A (α-gal A) were used to transduce HUH7 cells in duplicate. The GLA-codop vector is shown to mediate higher expression of the GLA protein.

FIG. 4 shows α-galactosidase A activity in adult Fabry mice (aged 3 months) or new born mice aged 1 week, 2 weeks or 3 weeks, following a single bolus tail vein injection of either 4e10 vg/mouse (=~$2 \times 10^{12}$ vg/kg) or 4e11 vg/mouse (=~$2 \times 10^{13}$ vg/kg) of AAV8 pseudotyped scAAV-GLA-codop. Activities were determined at 3 months after gene transfer when transgene expression is expected to have peaked. Data was collected at the time of a terminal bleed (plasma levels).

FIG. 5 shows α-galactosidase A activity in adult Fabry mice (aged 3 months) or new born mice aged 1 week, 2 weeks or 1 month, following a single bolus tail vein injection of either 4e10 vg/mouse (=~$2 \times 10^{12}$ vg/kg) or 4e11vg/mouse (=~$2 \times 10^{13}$ vg/kg) of AAV8 pseudotyped scAAV-GLA-codop. Activities were determined at 3 months after gene transfer when transgene expression is expected to have peaked. Data was collected in "real time" using blood spots.

Figure 8:
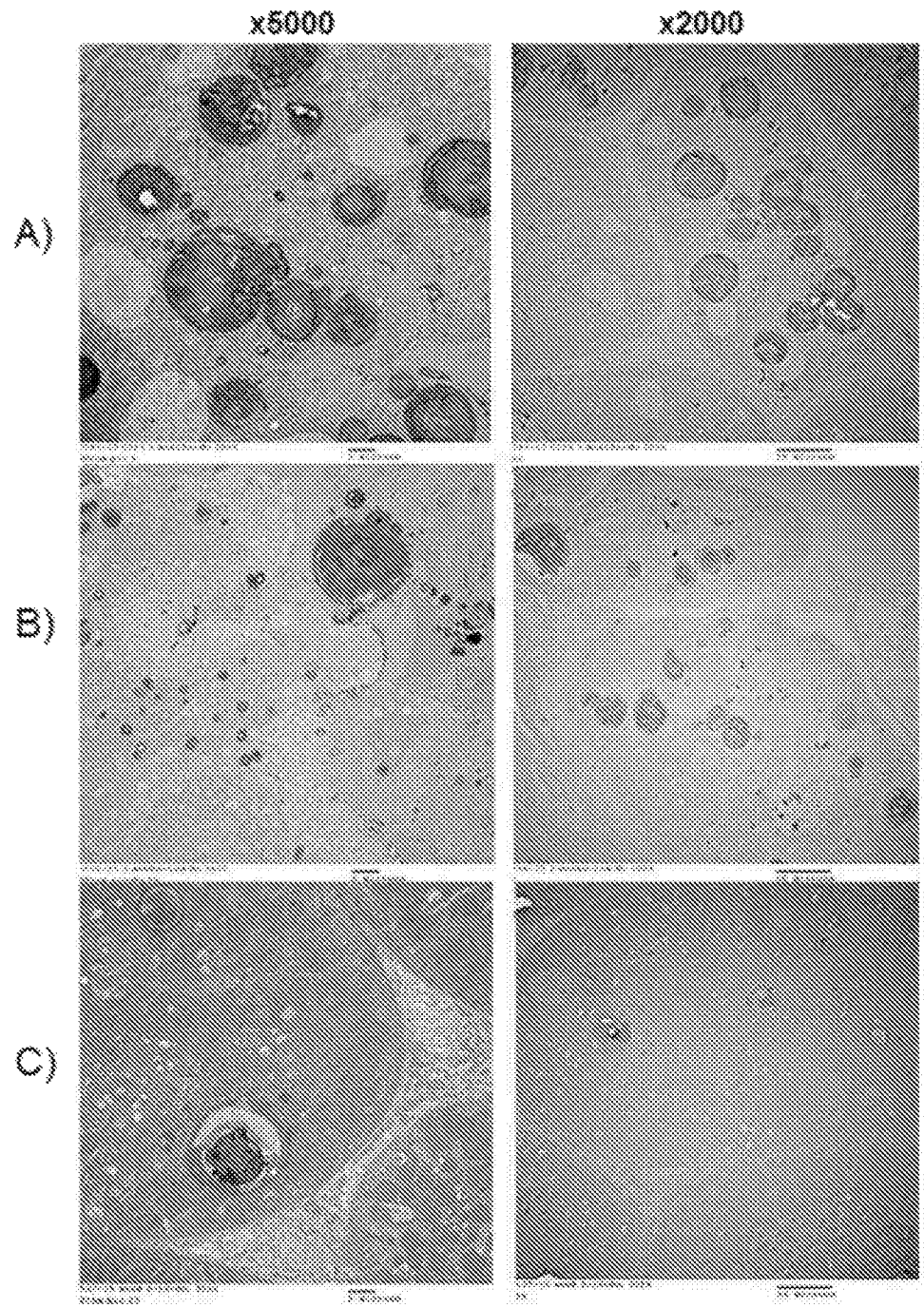

FIG. 8 shows electron micrographs of glycosphingolipid depositions in kidneys of α-GLA knockout mice following early stage i.p. injection of vector. A) untreated, B) AAV treated mice at the age of one week with low dose (2e12 vg/kg) and C) high dose (2e13 vg/kg). Treated mice were culled 5 months post-i.p. injection (magnifications: ×5000 and ×2000).

Figure 9:
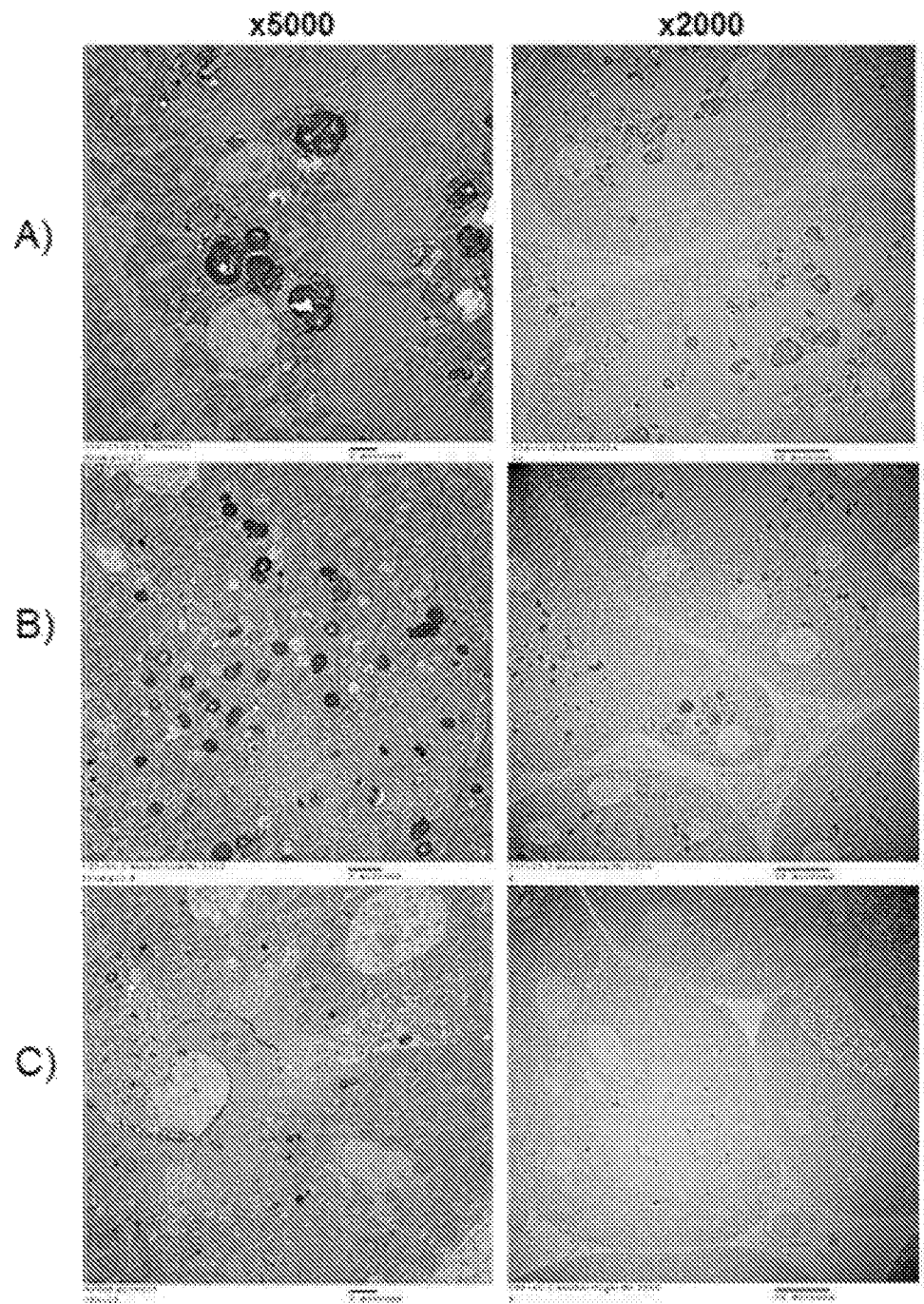

FIG. 9 shows electron micrographs of glycosphingolipid depositions in kidneys of α-GLA knockout mice following intermediate stage i.p. injection of vector. A) untreated, B) AAV treated mice at the age of 3 weeks of age with low dose (2e12 vg/kg) and C) high dose (2e13 vg/kg). Treated mice were culled one month post-i.p. injection (magnifications: ×5000 and ×2000).

Figure 10:
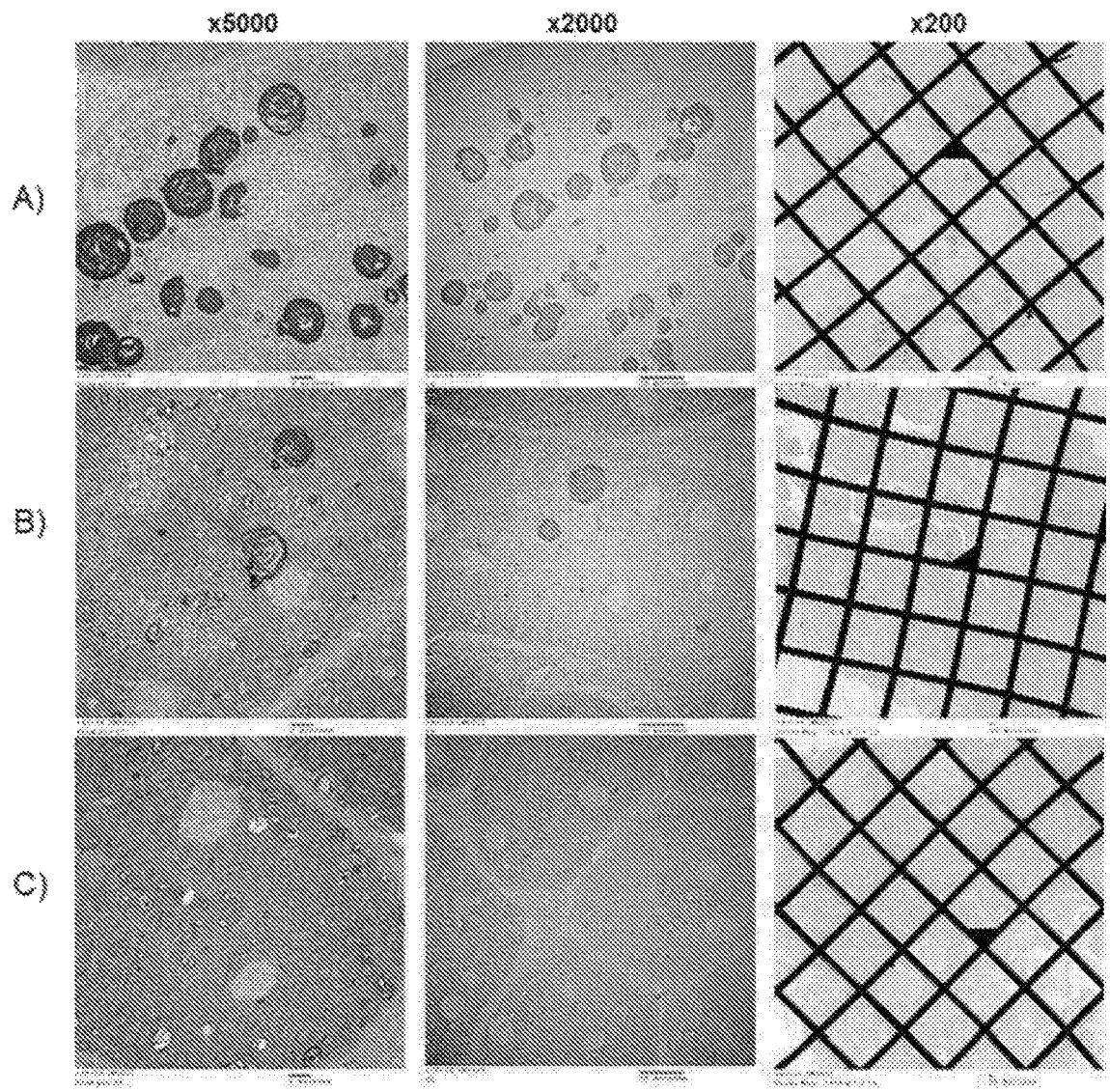

FIG. 10 shows electron micrographs of glycosphingolipid depositions in kidneys of α-GLA knockout mice following intermediate stage i.v. injection of vector. A) untreated, B) AAV treated mice at the age of one month with low dose (2e12 vg/kg) and C) high dose (2e13 vg/kg). Treated mice were culled 10 months post-i.v. injection (magnifications: ×5000, ×2000 and ×200).

Figure 11:
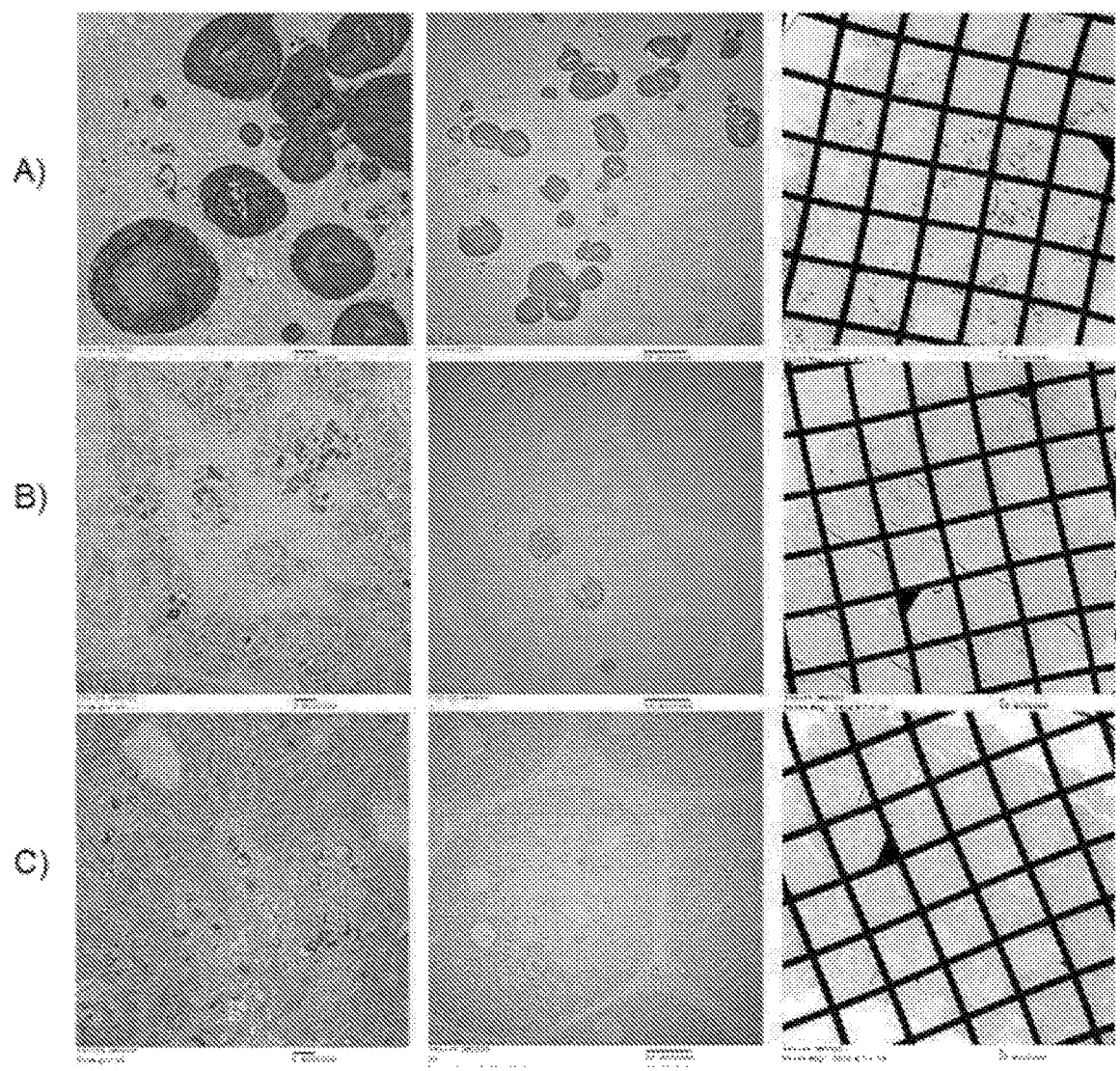

FIG. 11 shows electron micrographs of glycosphingolipid depositions in kidneys of α-GLA knockout mice following late stage i.v. injection of vector. A) untreated, B) AAV treated mice at the age of 3 month with low dose (2e12 vg/kg) and C) high dose (2e13 vg/kg). Treated mice were culled 13 months post-i.v. injection (magnifications: ×5000, ×2000 and ×200).

SUMMARY

The overriding goal of the inventors' research program is to establish a cure for Fabry disease that is safe, effective and widely available. In pursuit of this goal, the inventors have developed a liver directed AAV gene transfer approach with a unique codon optimised α-galactosidase A sequence.

The advantages of the present invention are that:
1. A single peripheral vein infusion of AAV encoding α-galactosidase A can result in long-term expression of α-galactosidase A in patients with Fabry disease. Stable long-term expression of α-galactosidase A following AAV mediated gene transfer, will:
   a. exert more a pronounced clinic benefit than possible with enzyme replacement therapy (ERT) thereby improving the prospects of preventing end organ damage and improvement in life expectancy of patients with Fabry disease;

b. eliminate the need for regular life-long infusion of α-galactosidase A thus improving quality of life; and
c. result in a potential saving to the NHS from a reduction/elimination of the need for expensive ERT
2. More potent expression from the codon optimised expression cassette resulting in a therapeutic benefit from using lower doses of AAV vector extracted in RIPA buffer with protease and phosphatase inhibitors added (Sigma-Aldrich).

Electron Microscopy Analysis

The ultrastructure of the mouse renal parenchyma was assessed by high resolution electron microscopy at various time points following gene transfer of codon-optimised α-galactosidase A. Vector was administered at a low dose (2e12 vg/kg) or at a high dose (2e13 vg/kg).

| Age | Early stage: i.p. injection | Intermediate stage: i.p. injection | Intermediate stage: i.v. injection | Late stage: i.v. injection |
| --- | --- | --- | --- | --- |
| α-GLA A KO mice received high and low dose of scAAV-LP1-GLAcod at the age of: | 1 to 2 weeks They were culled 5 months post i.p. injection. N = 6 for each group | 3 weeks They were culled one month post i.p. injection. N = 3 for each group | 1 month They were culled 10 months post i.v. injection. N = 3 for each group | 3 months They were culled 13 months post i.v. injection. N = 3 for each group |

3. Continuous higher plasma levels of α-galactosidase A following AAV mediated gene transfer and as such improved prospects of correcting pathology within the central nervous system and
4. Expression of α-galactosidase A from the liver will reduce the risk of developing neutralising antibodies to this protein which occurs in between 55-88% of patients after ERT.

The inventors have observed scAAV8-mediated gene transfer in adult (3 month old) and new born (2 days old) Fabry model mice resulting in levels of α-gal A that are substantially higher than physiological levels associated with uptake of this enzyme in major organs, thus raising the possibility of ameliorating the disease phenotype in patients with Fabry disease. No immunological responses to the protein have been observed following liver mediated transgene expression including in animals that received the vector at an early age and consequently had low levels of α-gal A expression, most likely reflecting the loss of episomally maintained AAV vector genome as the liver continues to grow to adult size.

Materials and Methods scAAV8 vectors expressing wild type (WT-GLA) and codon-optimised (codop-GLA) α-galactosidase A were transduced into HUH7 cells, a liver carcinoma cell line to assess potency. In brief, HUH7 cells cultured in DMEM with 10% FBS and plated at $5\times10^4$ cells per well in a 6-well culture plate were washed twice with OPTIMEM medium (Life Technologies), and then transduced with AAV vector. After 72 hours, cells were harvested for extraction of DNA, RNA or protein. DNA extraction was performed using a DNEasy Blood and Tissue Kit (Qiagen), and genome copy number calculated using a QPCR method and transgene specific primers as well as a cellular housekeeping gene (mouse or human GAPDH or beta-actin). A standard curve was set up during QPCR which allowed calculation of the genome copy number of the AAV vector. The host genome copy number was calculated by determining the concentration of genomic DNA following extraction, and assuming that the DNA content of each cell was 6.6 pg. By dividing these two values, the vector genome copy per host cell was calculated. RNA extraction was performed using Trizol (Life Technologies) and carried out using the manufacturer's instructions, and cDNA generated using Superscript II (Life Technologies). QRTPCR was performed using primers specific to either the endogenous or codon-optimized form of α-galactosidase A. For western blotting, the cells were Mice were killed at various time points after gene transfer. Kidneys were removed and fixed in 10% neutral buffered formalin, methyl Carnoy's solution and small blocks were fixed with 2.5% glutaraldehyde and 2% paraformaldehyde, followed by postfixation in 1% osmium tetroxide, and embedded in Epon using a standard procedure. Epon-embedded blocks were cut at 80 nm with a diamond knife. Then ultrathin sections were double-stained with uranyl acetate and lead citrate for electron microscopy. The same block faces were cut at 1 μm with a sapphire knife replacing a diamond knife. Sections were examined in an H-7650 electron microscope.

Results

Figure 1:
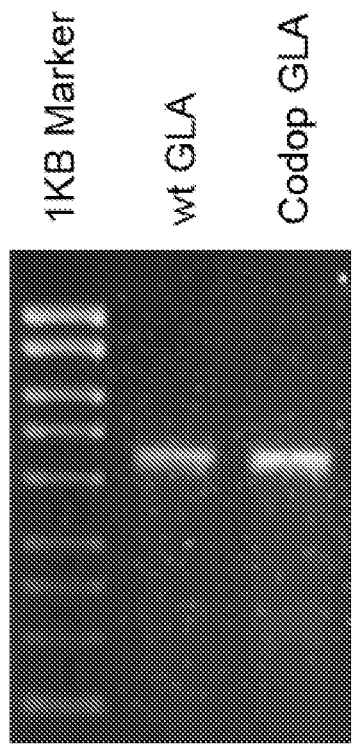
Figure 2:
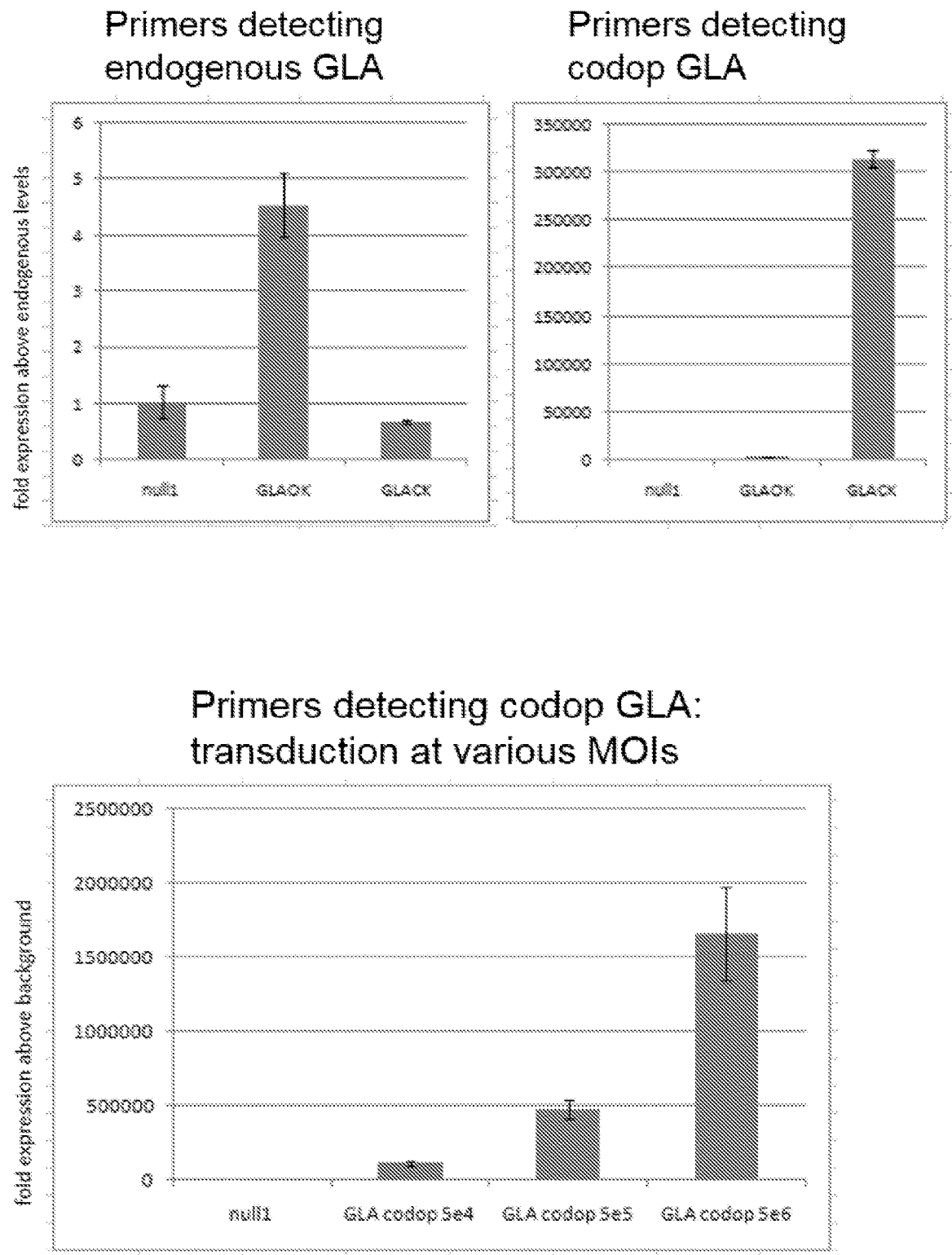
Figure 3:
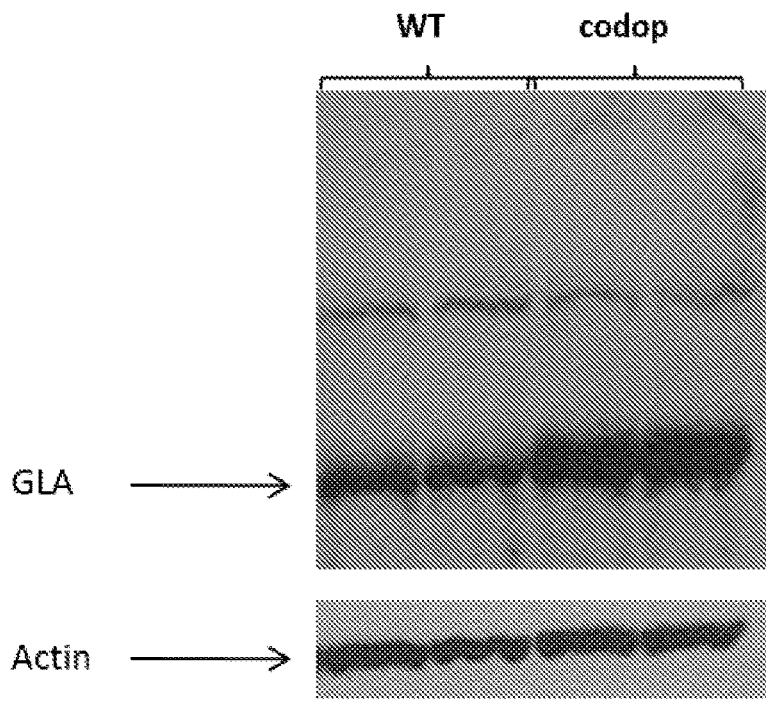

An initial evaluation has shown that transduction of hepatocytes with an AAV vector encoding codon optimised α-galactosidase A under the control of a liver specific promoter resulted in expression of transgenic α-galactosidase A at a level that was 4 fold higher than that observed with an identical construct containing wild-type α-galactosidase A cDNA, which was unexpected based on prior art (FIGS. 2 and 3).

Figure 4:
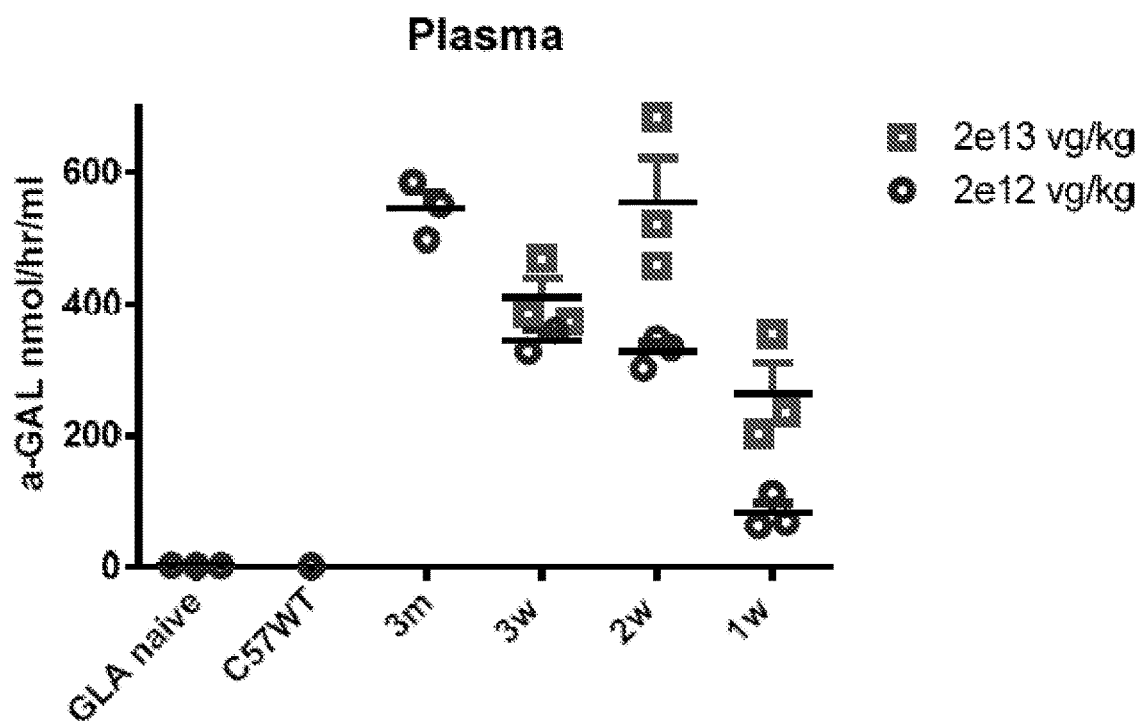
Figure 5:
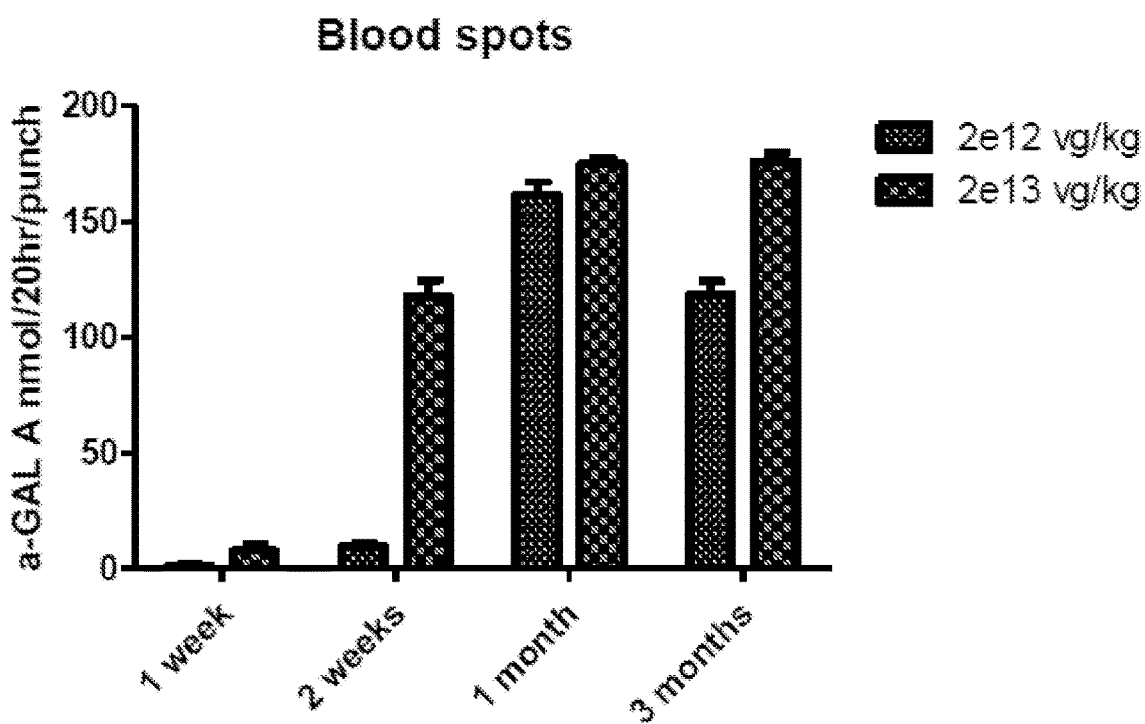

Fabry model mice were bred from C57BL/6 hemizygous male mice (0/−) and homozygous female mice (−/−) obtained from Kulkarni (T. Ohshima et al., Proc. Natl. Acad. Sci. USA, 94 (1997), pp. 2540-2544). Adult Fabry mice (aged 3 months) received a single bolus tail vein injection of either 4e10 vg/mouse (=~$2\times10^{12}$ vg/kg) or 4e11 vg/mouse (=~$2\times10^{13}$ vg/kg) of AAV8 pseudotyped scAAV-GLA-codop based on validated q-PCR assay and gel based quantitation assays. New born mice aged 1 week, 2 weeks or 3 weeks were given the same dose of vector, which was injected intraperitoneally. Blood samples were collected from the tail vein every 2 weeks thereafter. α-galactosidase A activities were determined by a functional assay as described above at the time of a terminal bleed (plasma levels) which was performed at 3 months after gene transfer when transgene expression is expected to have peaked (FIG. 4). α-galactosidase A activity level was also assessed in "real time" using the blood spots method (FIG. 5) as this requires smaller samples volumes (usually 20 μl of blood).

Figure 6:
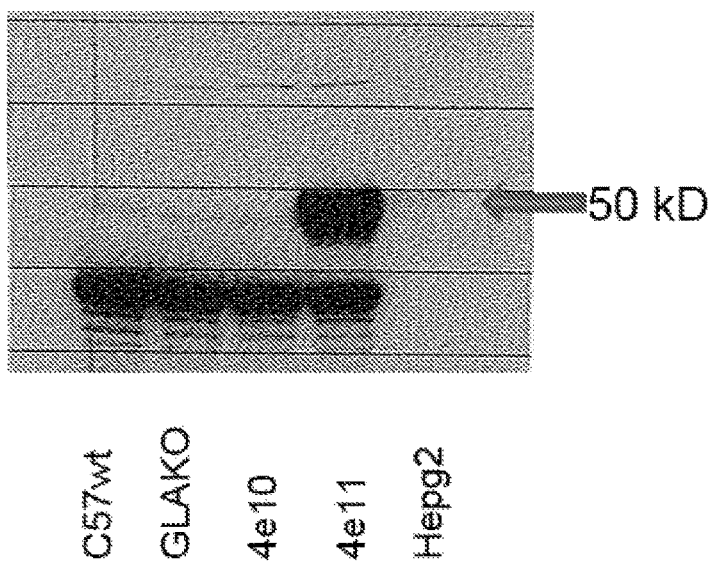
FIG. 6 shows Western blot analysis of liver from transduced animals. α-galactosidase A was expressed at high level following transduction with a dose of 4e11 vg/mouse but not following transduction with a dose of 4e10 vg/mouse.
Figure 7:
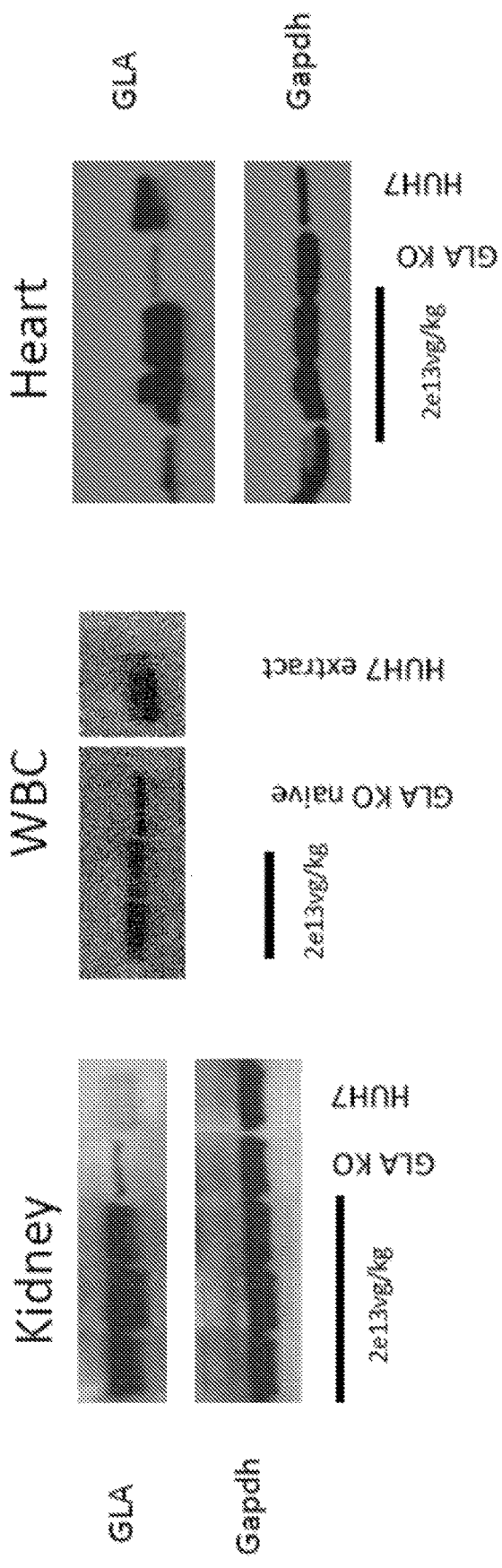
FIG. 7 shows Western blot analysis of α-galactosidase A expression in kidney, white blood cells (WBC) and heart from transduced animals.

High level of functional α-galactosidase A active was observed in all cohorts (N=4 animals/group) of mice regardless of whether the vector was administered in adult mice (3 months=3M) or in the early postnatal period between weeks 1-3 (single bolus injection at 1W, 2W, 3W). The activity levels were higher in animals that received $2\times10^{12}$ vg/kg of vector at 3 months with mean±SD=544 nmol/hr/ml. The levels in the animals injected with the same dose of vector but at 1 week after birth was 7 fold lower at 80 nmol/hr/ml. This is still almost 4 fold higher than normal levels in humans which has a range of 4.0-21.9 nmol/hr/ml. In the homozygote Fabry mice activity levels of 0-0.9 nmol/hr/ml were observed, whilst the heterozygote animals had levels that approached ~7.4 nmol/hr/ml. Therefore post gene transfer, an increase in α-galactosidase A activity of between 4-26 fold was observed. The levels observed with the blood spot assay were somewhat lower but this analysis confirmed dose dependent increase in α-galactosidase A activity in adults mice which was 118±6 and 176±4 nmol/hr/ml for the low and high dose cohorts respectively. Similar levels were observed in the cohort that received vector at 1 month of age. Animals transduced at 2 weeks after birth had α-galactosidase A activity of 10±2 and 117±7 nmol/hr/ml for the low and high dose cohorts respectively. In contrast the animals that received vector at 1 week of age had the lowest level of α-galactosidase A activity of 2±0.4 and 8±3 nmol/hr/ml following intraperitoneal administration of $2\times10^{12}$ or $2\times10^{13}$ vg/kg dose levels respectively. The inventors next assessed α-galactosidase A levels in major organs. Western blot analysis of liver from animals following transduction with a dose of 4e11 vg/mouse showed high levels of endogenous human α-galactosidase A expression (FIG. 6) but not in an animal transduced with 4e10 vg/mouse. In the 4e11 vg/mouse (=2e13 vg/kg) transduced animal, the white blood cells (WBC) showed presence of human α-galactosidase A suggesting uptake from plasma. In fact this was a consistent finding in other tissues including the kidneys and the heart (FIG. 7). Following gene transfer, levels of α-galactosidase A were comparable to those seen in wild type C57B16 mice, suggesting expression at levels approaching 100% of physiological levels. This is an unexpected finding based on our experience with enzyme replacement therapy. This therefore suggests continuous long term expression of α-galactosidase A following AAV mediated gene transfer promotes uptake of α-galactosidase A in critical organs that are affected in Fabry disease. The failure of these critical organs is the reason for reduced life expectancy in patients with Fabry disease and presents questions on the efficacy of enzyme replacement therapy.

Kidney involvement is a prominent feature of Fabry disease resulting from accumulations of neutral glycosphingolipid, mainly globotriaosylceramide (Gb3). Therefore the ultrastructure of the mouse renal parenchyma was assessed by high resolution electron microscopy. In untreated Fabry mice the podocytes formed foot process fusion and a storage process occurred with Gb3 accumulation, while filtration slits formed multivesicular bodies and degraded, and the slits diaphragm formed a complex. When such phenomena occur, proteinuria and glomerulosclerosis can develop. Following AAV8 pseudotyped scAAV-GLA-codop administration during the perinatal period, at 1 month after birth or at 3 months after birth (when renal pathology is established in untreated animals), a dose dependent but profound removal of lipid accumulation from the whole of the renal parenchyma was observed resulting in normal renal architecture (FIGS. 8-11). Hence, the $2\times10^{11}$ and $2\times10^{12}$ vg/kg dose levels could both deplete the accumulated Gb3 and prevent its re-accumulation in mice as illustrated by ultrastructural findings of fewer, smaller, or less dense lysosomes in the renal tissues of all groups of treated mice. These findings suggest that α-Gal A is readily endocytosed into endosomes for subsequent processing by lysosomes containing the substrate in the kidneys.

Sequences

SEQ ID NO. 1: nucleotide sequence of codon optimised α-galactosidase A.

SEQ ID NO. 2: nucleotide sequence of promoter HLP2.

SEQ ID NO. 3: nucleotide sequence of vector construct including promoter and codon optimised α-galactosidase A sequence (scAAV8-LP1-GLAco). This sequence contains the LP1 promoter. The codon optimised α-galactosidase A sequence is at bases 722-2011.

The invention claimed is:

1. A nucleic acid molecule comprising a nucleotide sequence encoding a polypeptide having α-galactosidase A activity wherein the nucleotide sequence has at least 91% identity to the nucleotide sequence of SEQ ID NO: 1.

2. The nucleic acid molecule of claim 1, wherein the nucleotide sequence has at least 95% identity to the nucleotide sequence of SEQ ID NO: 1.

3. The nucleic acid molecule of claim 1, wherein the nucleotide sequence has the nucleotide sequence of SEQ ID NO: 1.

4. A vector, a host cell, a transgenic animal, or a pharmaceutical composition comprising the nucleic acid molecule of claim 1.

5. The vector of claim 4, wherein the nucleotide sequence is operably linked to a liver specific promoter.

6. The vector of claim 4, wherein the vector is an AAV vector.

7. The vector of claim 4, wherein the vector is a single stranded vector.

8. The vector of claim 4, wherein the vector comprises a nucleotide sequence having at least 90% identity to the nucleotide sequence of SEQ ID NO: 3.

9. The vector of claim 4, wherein the vector comprises a nucleotide sequence having the nucleotide sequence of SEQ ID NO: 3.

10. The vector of claim 4, wherein the vector comprises a nucleotide sequence having at least 95% identity to the nucleotide sequence of SEQ ID NO: 3.

11. The vector of claim 4, wherein the vector comprises a nucleotide sequence having at least 98% identity to the nucleotide sequence of SEQ ID NO: 3.

12. The nucleic acid molecule of claim 1, wherein the nucleotide sequence has at least 98% identity to the nucleotide sequence of SEQ ID NO: 1.

13. The nucleic acid molecule of claim 1, wherein the nucleotide sequence has at least 99% identity to the nucleotide sequence of SEQ ID NO: 1.

14. The nucleic acid molecule of claim 1, wherein the nucleotide sequence has at least 92% identity to the nucleotide sequence of SEQ ID NO: 1.

15. The nucleic acid molecule of claim 1, wherein the nucleotide sequence has at least 93% identity to the nucleotide sequence of SEQ ID NO: 1.

16. The nucleic acid molecule of claim 1, wherein the nucleotide sequence has at least 94% identity to the nucleotide sequence of SEQ ID NO: 1.

17. The nucleic acid molecule of claim 1, wherein the nucleotide sequence has at least 96% identity to the nucleotide sequence of SEQ ID NO: 1.

18. The nucleic acid molecule of claim 1, wherein the nucleotide sequence has at least 97% identity to the nucleotide sequence of SEQ ID NO: 1.

* * * * *